US011225678B2

United States Patent
Anderson et al.

(10) Patent No.: US 11,225,678 B2
(45) Date of Patent: Jan. 18, 2022

(54) FERMENTATION METHODS FOR PRODUCING STEVIOL GLYCOSIDES WITH MULTI-PHASE FEEDING

(71) Applicant: CARGILL, INCORPORATED, Wayzata, MN (US)

(72) Inventors: James C. Anderson, Eden Prairie, MN (US); Ting Liu Carlson, Marietta, SC (US); Arlene M. Fosmer, Eden Prairie, MN (US)

(73) Assignee: Cargill, Incorporated, Wayzata, MN (US)

( * ) Notice: Subject to any disclaimer, the term of this patent is extended or adjusted under 35 U.S.C. 154(b) by 176 days.

(21) Appl. No.: 15/578,179

(22) PCT Filed: May 27, 2016

(86) PCT No.: PCT/US2016/034826
§ 371 (c)(1),
(2) Date: Nov. 29, 2017

(87) PCT Pub. No.: WO2016/196368
PCT Pub. Date: Dec. 8, 2016

(65) Prior Publication Data
US 2018/0148750 A1    May 31, 2018

Related U.S. Application Data

(60) Provisional application No. 62/168,372, filed on May 29, 2015.

(51) Int. Cl.
*C12P 15/00*    (2006.01)
*C12P 1/02*    (2006.01)
(Continued)

(52) U.S. Cl.
CPC .............. *C12P 15/00* (2013.01); *C12N 1/185* (2021.05); *C12N 15/74* (2013.01); *C12N 15/81* (2013.01); *C12P 1/02* (2013.01); *C12R 2001/865* (2021.05)

(58) Field of Classification Search
None
See application file for complete search history.

(56) References Cited

U.S. PATENT DOCUMENTS 10,612,065 B2    4/2020    Anderson et al.
2002/0184700 A1    11/2002    Andersen et al.
(Continued)

FOREIGN PATENT DOCUMENTS

EP    1305440    6/2010
WO    WO0125467    4/2001
(Continued)

OTHER PUBLICATIONS

International Search Report of PCT/US2016/034826 dated Sep. 13, 2016 (4 pgs.).
(Continued)

*Primary Examiner* — Richard C Ekstrom
(74) *Attorney, Agent, or Firm* — McDonnell Boehnen Hulbert & Berghoff LLP

(57) ABSTRACT

Disclosed are methods for producing steviol glycosides, such as rebaudioside D and rebaudioside M, using engineered yeast. The methods include at least two phases: first and second phases where a glucose-containing feed composition is provided to the medium in different modes of feeding in each phase, such as variable feeding and then constant feeding. The two phase feeding can result in a growth rate that is slower in the second phase than in the first
(Continued)

phase, and consequently increased steviol glycoside production rates, reduced fermentation times, and reduced biomass concentrations.

17 Claims, 4 Drawing Sheets

Specification includes a Sequence Listing.

(51) Int. Cl.
| | |
|---|---|
| *C12N 1/18* | (2006.01) |
| *C12N 15/74* | (2006.01) |
| *C12N 15/81* | (2006.01) |
| *C12R 1/865* | (2006.01) |

(56) References Cited

U.S. PATENT DOCUMENTS

| | | | |
|---|---|---|---|
| 2006/0083838 | A1 | 4/2006 | Jackson et al. |
| 2006/0134742 | A1 | 6/2006 | Brazeau et al. |
| 2010/0184133 | A1 | 7/2010 | Norgaard et al. |
| 2011/0081697 | A1 | 4/2011 | Liu et al. |
| 2011/0189717 | A1 | 8/2011 | Ajikumar et al. |
| 2012/0164678 | A1 | 6/2012 | Stephanopoulos et al. |
| 2012/0165562 | A1 | 6/2012 | Hattendorf et al. |
| 2013/0071339 | A1 | 3/2013 | Markosyan et al. |
| 2013/0171328 | A1 | 7/2013 | Kishore et al. |
| 2014/0329281 | A1 | 11/2014 | Houghton-Larsen et al. |
| 2014/0357588 | A1 | 12/2014 | Markosyan et al. |
| 2015/0031868 | A1 | 1/2015 | Lehmann et al. |
| 2015/0037462 | A1 | 2/2015 | Markosyan et al. |
| 2016/0102331 | A1 | 4/2016 | Boer et al. |
| 2016/0153017 | A1 | 6/2016 | Van Der Hoeven et al. |
| 2016/0177360 | A1 | 6/2016 | Boer et al. |
| 2016/0348192 | A1 | 12/2016 | Tilloy et al. |
| 2018/0073050 | A1 | 3/2018 | Boer et al. |
| 2018/0148750 | A1* | 5/2018 | Anderson ............... C12P 15/00 |
| 2018/0155751 | A1 | 6/2018 | Anderson et al. |
| 2018/0163244 | A1 | 6/2018 | Anderson et al. |
| 2018/0230504 | A1 | 8/2018 | Anderson et al. |

FOREIGN PATENT DOCUMENTS

| | | |
|---|---|---|
| WO | WO2006045023 | 4/2006 |
| WO | WO2009140394 | 11/2009 |
| WO | WO2011153378 | 12/2011 |
| WO | WO2013022989 | 2/2013 |
| WO | WO2013096420 | 6/2013 |
| WO | WO2013110673 | 8/2013 |
| WO | 2014122227 A2 | 8/2014 |
| WO | WO2014122328 | 8/2014 |
| WO | 2014145521 A2 | 9/2014 |
| WO | WO2014191580 | 12/2014 |
| WO | WO2014191581 | 12/2014 |
| WO | WO2014193888 | 12/2014 |
| WO | WO2014193934 | 12/2014 |
| WO | WO2015007748 | 1/2015 |
| WO | WO2015011209 | 1/2015 |
| WO | WO2015014959 | 2/2015 |
| WO | WO2015014969 | 2/2015 |
| WO | WO2016196321 | 12/2016 |
| WO | WO2016196345 | 12/2016 |
| WO | WO2017024313 | 2/2017 |

OTHER PUBLICATIONS

Chisti, Y. "Fermentation (Industrial): Basic Considerations" in: "Encyclopedia of Food Microbiology" (1999 ed.), pp. 663-674 (1999).
International Preliminary Report on Patentability from then International Search Authority for International Application No. PCT/US2016/034826; dated Aug. 20, 2017, pp. 1-13.
"Nomenclature committee of the international union of biochemistry and molecular biology (NC-IUBMB), Enzyme Supplement 5 (1999)," Eur J Biochem. 264(2):610-50, (1999).
Anderlei et al., "Device for sterile online measurement of the oxygen transfer rate in shaking flasks," Biochemical Engineering Journal 3478:1-6, (2000).
Barrett, "Nomenclature Committee of the International Union of Biochemistry and Molecular Biology (NC-IUBMB). Enzyme nomenclature. Recommendations 1992. Supplement 2: corrections and additions (1994)," Eur. J. Biochem., 232:1-6, (1995).
Barrett, "Nomenclature Committee of the International Union of Biochemistry and Molecular Biology (NC-IUBMB). Enzyme nomenclature. Recommendations 1992. Supplement 3: corrections and additions (1995)," Eur J Biochem. 237(1):1-5, (1996).
Barrett, "Nomenclature Committee of the International Union of Biochemistry and Molecular Biology (NC-IUBMB). Enzyme Nomenclature. Recommendations 1992. Supplement 4: corrections and additions (1997)," Eur J Biochem. 250(1):1-6, (1997).
Chen et al., "The glucose RQ-feedback control leading to improved erythromycin production by a recombinant strain Saccharopolyspora erythraea ZL1004 and its scale-up to 372-m(3) fermenter," Bioprocess Biosyst Eng. 38(1):105-12 (2015).
Jasmin, et al., "The yield of experimental yeast populations declines during selection," Proc Biol Sci. 2012. vol. 279 (1746): p. 4382-8 (2012).
Jules, et al., "Two Distinct Pathways for Trehalose Assimilation in the Yeast *Saccaromyces cerevisiae*," Appl Environ C Microbiol., vol. 70(5), p. 2771-2778 (2004).
Li et al., "Phylogenetic analysis of the UDP-glycosyltransferase multigene family of *Arabidopsis thaliana*," J Biol Chem. 276(6):4338-43 (2001).
Lynd, et al., "Microbial cellulose utilization: fundamentals and biotechnology," Microbial. Mol. Biol. Rev., 66:506-577 (2002).
Ohta et al., "Characterization of Novel Steviol Glycosides from leaves of Stevia rebaudiana Morita", Journal of Applied Glycoscience, The Japanese Society of Applied Glycoscience, Aug. 17, 2010, Issue 57, pp. 199-209.
Prakash et al., "Isolation, characterization and sensory evaluation of a Hexa beta-D-glucopyranosyl diterpene from Stevia rebaudiana," Nat Prod Commun. 8(11):1523-6 (2013).
Prakash et al., "Catalytic hydrogenation of the sweet principles of Stevia rebaudiana, Rebaudioside B, Rebaudioside C, and Rebaudioside D and sensory evaluation of their reduced derivatives," Int J Mol Sci. 13(11):15126-36 (2012).
Tipton, "Nomenclature Committee of the International Union of Biochemistry and Molecular Biology (NC-IUBMB). Enzyme nomenclature. Recommendations 1992. Supplement: corrections and additions," Eur J Biochem., 223(1):1-5 (1994).
Verduyn, C. et al., "Effect of benzoic acid on metabolic fluxes in yeasts: a continuous-culture study on the regulation of respiration and alcoholic fermentation," Yeast 8, 501-517 (1992).
Kizer et al., "Application of functional genomics to pathway optimization for increased isoprenoid production," Appl Environ Microbiol.; 74(10):3229-41 (2008).
Prather et al., "De novo biosynthetic pathways: rational design of microbial chemical factories," Curr Opin Biotechnol. 19(5):468-74 (2008).
International Search Report issued by the International Searching Authority for International Application No. PCT/US2016/034728, dated Sep. 8, 2016 (4 pages).
International Preliminary Report on Patentability from then International Search Authority for International Application No. PCT/US2016/034728; dated Dec. 5, 2017, pp. 1-14.
Extended European Search Report and Opinion issued by the European Patent Office for European Application No. 16804137.4, dated Sep. 14, 2018 (pp. 1-8).
Examination Report issued by the European Patent Office for European Application No. 16804170.5, dated Aug. 23, 2019 (p. 1-5).
International Search Report issued by the International Searching Authority for International Application No. PCT/US201616/046072, dated Dec. 1, 2016 (4 pages).

(56) References Cited

OTHER PUBLICATIONS

International Preliminary Report on Patentability from then International Search Authority for International Application No. PCT/US201616/046072; dated Feb. 6, 2018, pp. 1-12.
Extended European Search Report and Opinion issued by the European Patent Office for European Application No. 16834005.7, dated Feb. 13, 2019 (p. 1-11).
Extended European Search Report and Opinion issued by the European Patent Office for European Application No. 16804170.5, dated Dec. 10, 2018 (p. 1).
Non-Final Office Action issued in U.S. Appl. No. 15/750,636; dated Apr. 18, 2019, pp. 1-8.
Final Office Action issued in U.S. Appl. No. 15/750,636; dated Oct. 7, 2019, pp. 1-12.
International Search Report and Written Opinion issued by the International Searching Authority for International Application No. PCT/EP2014/065858, dated Oct. 20, 2014 (12 pages).
International Preliminary Report on Patentability from the International Search Authority for International Application No. PCT/EP2014/065858, dated Jan. 1, 2016 (9 pages).
Examination Report issued by the European Patent Office for European Application No. 14741925.3, dated Mar. 14, 2017 (p. 1-10).
Examination Report issued by the European Patent Office for European Application No. 14741925.3, dated Feb. 26, 2018 (p. 1-3).
Non-Final Office Action issued in U.S. Appl. No. 15/578,125; dated May 21, 2019, pp. 1-14.
Final Office Action issued in U.S. Appl. No. 15/578,125; dated Oct. 8, 2019, pp. 1-16.
Non-Final Office Action issued in U.S. Appl. No. 14/906,497; dated Jul. 17, 2018 pp. 1-30.
Brandle & Telmer, "Steviol glycoside biosynthesis," Phytochemistry 68(14):1855-63 (2007).

Coelho, "Yarrowia lipolytica: An industrial workhorse," Current Research, Technology and Education Topics in Applied Microbiology and Microbial Biotechnology A. Méndez-Vilas (Ed.), 930-944 (2010).
Gonçalves, "Yarrowia Lipolytica and Its Multiple Applications in the Biotechnological Industry," The Scientific World Journal, vol. 2014, 1-14 (2014).
Kebabci et al., "Comparison of three Yarrowia lipolytica strains for lipase production: NBRC 1658, IFO 1195, and a local strain" Turk J Biol, 36 (2012) 15-24 (2012).
Kumar et al., "A comprehensive analysis of fifteen genes of steviol glycosides biosynthesis pathway in Stevia rebaudiana (Bertoni)" Gene 492:276-84 (Epub Oct. 20, 2011).
Li et al., "Production of Rebaudioside A from Stevioside Catalyzed by the Engineered *Saccharomyces cerevisiae*," Appl Biochem Biotechnol. 178(8):1586-98 (2016).
Moeller et al., "Optimization of Citric Acid Production from Glucose by Yarrowia lipolytica," Eng. Life Sci, 7(5):504-511 (2007).
International Search Report issued by the International Searching Authority for International Application No. PCT/US2016/034781, dated Aug. 29, 2016 (2 pages).
International Preliminary Report on Patentability from then International Search Authority for International Application No. PCT/US2016/034781; dated Aug. 3, 2016, pp. 1-9.
Extended European Search Report and Opinion issued by the European Patent Office for European Application No. 16804152.3, dated Nov. 6, 2018 (pp. 1-4).
Supplementary European Search Report and Opinion issued by the European Patent Office for European Application No. 16804152.3, dated Oct. 25, 2018 (pp. 1-2).
Non-Final Office Action issued in U.S. Appl. No. 15/578,154; dated Jul. 16, 2019, pp. 1-12.
Non-Final Office Action issued in U.S. Appl. No. 16/796,630; dated Sep. 25, 2020, pp. 1-14.
Final Office Action issued in U.S. Appl. No. 16/796,630; dated Jan. 14, 2021, pp. 1-6.

\* cited by examiner

SEQUENCE LISTING

<160> NUMBER OF SEQ ID NOS: 22

<210> SEQ ID NO 1
<211> LENGTH: 460
<212> TYPE: PRT
<213> ORGANISM: Stevia rebaudiana

<400> SEQUENCE: 1

```
Met Ala Glu Gln Gln Lys Ile Lys Lys Ser Pro His Val Leu Leu Ile
1               5                   10                  15

Pro Phe Pro Leu Gln Gly His Ile Asn Pro Phe Ile Gln Phe Gly Lys
            20                  25                  30

Arg Leu Ile Ser Lys Gly Val Lys Thr Thr Leu Val Thr Thr Ile His
        35                  40                  45

Thr Leu Asn Ser Thr Leu Asn His Ser Asn Thr Thr Thr Thr Ser Ile
    50                  55                  60

Glu Ile Gln Ala Ile Ser Asp Gly Cys Asp Glu Gly Gly Phe Met Ser
65                  70                  75                  80

Ala Gly Glu Ser Tyr Leu Glu Thr Phe Lys Gln Val Gly Ser Lys Ser
                85                  90                  95

Leu Ala Asp Leu Ile Lys Lys Leu Gln Ser Glu Gly Thr Thr Ile Asp
            100                 105                 110

Ala Ile Ile Tyr Asp Ser Met Thr Glu Trp Val Leu Asp Val Ala Ile
        115                 120                 125

Glu Phe Gly Ile Asp Gly Gly Ser Phe Phe Thr Gln Ala Cys Val Val
    130                 135                 140

Asn Ser Leu Tyr Tyr His Val His Lys Gly Leu Ile Ser Leu Pro Leu
145                 150                 155                 160

Gly Glu Thr Val Ser Val Pro Gly Phe Pro Val Leu Gln Arg Trp Glu
                165                 170                 175

Thr Pro Leu Ile Leu Gln Asn His Glu Gln Ile Gln Ser Pro Trp Ser
            180                 185                 190

Gln Met Leu Phe Gly Gln Phe Ala Asn Ile Asp Gln Ala Arg Trp Val
        195                 200                 205

Phe Thr Asn Ser Phe Tyr Lys Leu Glu Glu Glu Val Ile Glu Trp Thr
    210                 215                 220

Arg Lys Ile Trp Asn Leu Lys Val Ile Gly Pro Thr Leu Pro Ser Met
225                 230                 235                 240

Tyr Leu Asp Lys Arg Leu Asp Asp Lys Asp Asn Gly Phe Asn Leu
                245                 250                 255

Tyr Lys Ala Asn His His Glu Cys Met Asn Trp Leu Asp Asp Lys Pro
            260                 265                 270

Lys Glu Ser Val Val Tyr Val Ala Phe Gly Ser Leu Val Lys His Gly
        275                 280                 285

Pro Glu Gln Val Glu Glu Ile Thr Arg Ala Leu Ile Asp Ser Asp Val
    290                 295                 300

Asn Phe Leu Trp Val Ile Lys His Lys Glu Glu Gly Lys Leu Pro Glu
305                 310                 315                 320

Asn Leu Ser Glu Val Ile Lys Thr Gly Lys Gly Leu Ile Val Ala Trp
                325                 330                 335

Cys Lys Gln Leu Asp Val Leu Ala His Glu Ser Val Gly Cys Phe Val
            340                 345                 350

Thr His Cys Gly Phe Asn Ser Thr Leu Glu Ala Ile Ser Leu Gly Val
        355                 360                 365
```

```
Pro Val Val Ala Met Pro Gln Phe Ser Asp Gln Thr Thr Asn Ala Lys
    370                 375                 380

Leu Leu Asp Glu Ile Leu Gly Val Gly Val Arg Val Lys Ala Asp Glu
385                 390                 395                 400

Asn Gly Ile Val Arg Arg Gly Asn Leu Ala Ser Cys Ile Lys Met Ile
                405                 410                 415

Met Glu Glu Glu Arg Gly Val Ile Ile Arg Lys Asn Ala Val Lys Trp
            420                 425                 430

Lys Asp Leu Ala Lys Val Ala His Glu Gly Ser Ser Asp Asn
        435                 440                 445

Asp Ile Val Glu Phe Val Ser Glu Leu Ile Lys Ala
    450                 455                 460

<210> SEQ ID NO 2
<211> LENGTH: 481
<212> TYPE: PRT
<213> ORGANISM: Stevia rebaudiana

<400> SEQUENCE: 2

Met Asp Ala Met Ala Thr Thr Glu Lys Lys Pro His Val Ile Phe Ile
1               5                   10                  15

Pro Phe Pro Ala Gln Ser His Ile Lys Ala Met Leu Lys Leu Ala Gln
                20                  25                  30

Leu Leu His His Lys Gly Leu Gln Ile Thr Phe Val Asn Thr Asp Phe
            35                  40                  45

Ile His Asn Gln Phe Leu Glu Ser Ser Gly Pro His Cys Leu Asp Gly
        50                  55                  60

Ala Pro Gly Phe Arg Phe Glu Thr Ile Pro Asp Gly Val Ser His Ser
65                  70                  75                  80

Pro Glu Ala Ser Ile Pro Ile Arg Glu Ser Leu Leu Arg Ser Ile Glu
                85                  90                  95

Thr Asn Phe Leu Asp Arg Phe Ile Asp Leu Val Thr Lys Leu Pro Asp
            100                 105                 110

Pro Pro Thr Cys Ile Ile Ser Asp Gly Phe Leu Ser Val Phe Thr Ile
        115                 120                 125

Asp Ala Ala Lys Lys Leu Gly Ile Pro Val Met Met Tyr Trp Thr Leu
130                 135                 140

Ala Ala Cys Gly Phe Met Gly Phe Tyr His Ile His Ser Leu Ile Glu
145                 150                 155                 160

Lys Gly Phe Ala Pro Leu Lys Asp Ala Ser Tyr Leu Thr Asn Gly Tyr
                165                 170                 175

Leu Asp Thr Val Ile Asp Trp Val Pro Gly Met Glu Gly Ile Arg Leu
            180                 185                 190

Lys Asp Phe Pro Leu Asp Trp Ser Thr Asp Leu Asn Asp Lys Val Leu
        195                 200                 205

Met Phe Thr Thr Glu Ala Pro Gln Arg Ser His Lys Val Ser His His
    210                 215                 220

Ile Phe His Thr Phe Asp Glu Leu Glu Pro Ser Ile Ile Lys Thr Leu
225                 230                 235                 240

Ser Leu Arg Tyr Asn His Ile Tyr Thr Ile Gly Pro Leu Gln Leu Leu
                245                 250                 255

Leu Asp Gln Ile Pro Glu Glu Lys Lys Gln Thr Gly Ile Thr Ser Leu
            260                 265                 270

His Gly Tyr Ser Leu Val Lys Glu Glu Pro Glu Cys Phe Gln Trp Leu
        275                 280                 285
```

```
Gln Ser Lys Glu Pro Asn Ser Val Val Tyr Val Asn Phe Gly Ser Thr
    290                 295                 300

Thr Val Met Ser Leu Glu Asp Met Thr Glu Phe Gly Trp Gly Leu Ala
305                 310                 315                 320

Asn Ser Asn His Tyr Phe Leu Trp Ile Ile Arg Ser Asn Leu Val Ile
                325                 330                 335

Gly Glu Asn Ala Val Leu Pro Pro Glu Leu Glu His Ile Lys Lys
            340                 345                 350

Arg Gly Phe Ile Ala Ser Trp Cys Ser Gln Glu Lys Val Leu Lys His
        355                 360                 365

Pro Ser Val Gly Gly Phe Leu Thr His Cys Gly Trp Gly Ser Thr Ile
    370                 375                 380

Glu Ser Leu Ser Ala Gly Val Pro Met Ile Cys Trp Pro Tyr Ser Trp
385                 390                 395                 400

Asp Gln Leu Thr Asn Cys Arg Tyr Ile Cys Lys Glu Trp Glu Val Gly
                405                 410                 415

Leu Glu Met Gly Thr Lys Val Lys Arg Asp Glu Val Lys Arg Leu Val
            420                 425                 430

Gln Glu Leu Met Gly Glu Gly His Lys Met Arg Asn Lys Ala Lys
        435                 440                 445

Asp Trp Lys Glu Lys Ala Arg Ile Ala Ile Ala Pro Asn Gly Ser Ser
    450                 455                 460

Ser Leu Asn Ile Asp Lys Met Val Lys Glu Ile Thr Val Leu Ala Arg
465                 470                 475                 480

Asn

<210> SEQ ID NO 3
<211> LENGTH: 458
<212> TYPE: PRT
<213> ORGANISM: Stevia rebaudiana

<400> SEQUENCE: 3

Met Glu Asn Lys Thr Glu Thr Thr Val Arg Arg Arg Arg Ile Ile
1               5                   10                  15

Leu Phe Pro Val Pro Phe Gln Gly His Ile Asn Pro Ile Leu Gln Leu
            20                  25                  30

Ala Asn Val Leu Tyr Ser Lys Gly Phe Ser Ile Thr Ile Phe His Thr
        35                  40                  45

Asn Phe Asn Lys Pro Lys Thr Ser Asn Tyr Pro His Phe Thr Phe Arg
    50                  55                  60

Phe Ile Leu Asp Asn Asp Pro Gln Asp Glu Arg Ile Ser Asn Leu Pro
65              70                  75                  80

Thr His Gly Pro Leu Ala Gly Met Arg Ile Pro Ile Ile Asn Glu His
            85                  90                  95

Gly Ala Asp Glu Leu Arg Arg Glu Leu Glu Leu Leu Met Leu Ala Ser
        100                 105                 110

Glu Glu Asp Glu Glu Val Ser Cys Leu Ile Thr Asp Ala Leu Trp Tyr
    115                 120                 125

Phe Ala Gln Ser Val Ala Asp Ser Leu Asn Leu Arg Arg Leu Val Leu
        130                 135                 140

Met Thr Ser Ser Leu Phe Asn Phe His Ala His Val Ser Leu Pro Gln
145                 150                 155                 160

Phe Asp Glu Leu Gly Tyr Leu Asp Pro Asp Asp Lys Thr Arg Leu Glu
                165                 170                 175
```

-continued

Glu Gln Ala Ser Gly Phe Pro Met Leu Lys Val Lys Asp Ile Lys Ser
            180                 185                 190

Ala Tyr Ser Asn Trp Gln Ile Leu Lys Glu Ile Leu Gly Lys Met Ile
        195                 200                 205

Lys Gln Thr Lys Ala Ser Ser Gly Val Ile Trp Asn Ser Phe Lys Glu
    210                 215                 220

Leu Glu Glu Ser Glu Leu Glu Thr Val Ile Arg Glu Ile Pro Ala Pro
225                 230                 235                 240

Ser Phe Leu Ile Pro Leu Pro Lys His Leu Thr Ala Ser Ser Ser Ser
                245                 250                 255

Leu Leu Asp His Asp Arg Thr Val Phe Gln Trp Leu Asp Gln Gln Pro
                260                 265                 270

Pro Ser Ser Val Leu Tyr Val Ser Phe Gly Ser Thr Ser Glu Val Asp
            275                 280                 285

Glu Lys Asp Phe Leu Glu Ile Ala Arg Gly Leu Val Asp Ser Lys Gln
        290                 295                 300

Ser Phe Leu Trp Val Val Arg Pro Gly Phe Val Lys Gly Ser Thr Trp
305                 310                 315                 320

Val Glu Pro Leu Pro Asp Gly Phe Leu Gly Glu Arg Gly Arg Ile Val
                325                 330                 335

Lys Trp Val Pro Gln Gln Glu Val Leu Ala His Gly Ala Ile Gly Ala
                340                 345                 350

Phe Trp Thr His Ser Gly Trp Asn Ser Thr Leu Glu Ser Val Cys Glu
            355                 360                 365

Gly Val Pro Met Ile Phe Ser Asp Phe Gly Leu Asp Gln Pro Leu Asn
        370                 375                 380

Ala Arg Tyr Met Ser Asp Val Leu Lys Val Gly Val Tyr Leu Glu Asn
385                 390                 395                 400

Gly Trp Glu Arg Gly Glu Ile Ala Asn Ala Ile Arg Arg Val Met Val
                405                 410                 415

Asp Glu Glu Gly Glu Tyr Ile Arg Gln Asn Ala Arg Val Leu Lys Gln
            420                 425                 430

Lys Ala Asp Val Ser Leu Met Lys Gly Gly Ser Ser Tyr Glu Ser Leu
        435                 440                 445

Glu Ser Leu Val Ser Tyr Ile Ser Ser Leu
    450                 455

<210> SEQ ID NO 4
<211> LENGTH: 473
<212> TYPE: PRT
<213> ORGANISM: Stevia rebaudiana

<400> SEQUENCE: 4

Met Ala Thr Ser Asp Ser Ile Val Asp Asp Arg Lys Gln Leu His Val
1               5                   10                  15

Ala Thr Phe Pro Trp Leu Ala Phe Gly His Ile Leu Pro Tyr Leu Gln
            20                  25                  30

Leu Ser Lys Leu Ile Ala Glu Lys Gly His Lys Val Ser Phe Leu Ser
        35                  40                  45

Thr Thr Arg Asn Ile Gln Arg Leu Ser Ser His Ile Ser Pro Leu Ile
    50                  55                  60

Asn Val Val Gln Leu Thr Leu Pro Arg Val Gln Glu Leu Pro Glu Asp
65                  70                  75                  80

Ala Glu Ala Thr Thr Asp Val His Pro Glu Asp Ile Pro Tyr Leu Lys

```
            85                  90                  95
Lys Ala Ser Asp Gly Leu Gln Pro Glu Val Thr Arg Phe Leu Glu Gln
        100                 105                 110

His Ser Pro Asp Trp Ile Ile Tyr Asp Tyr Thr His Tyr Trp Leu Pro
        115                 120                 125

Ser Ile Ala Ala Ser Leu Gly Ile Ser Arg Ala His Phe Ser Val Thr
130                 135                 140

Thr Pro Trp Ala Ile Ala Tyr Met Gly Pro Ser Ala Asp Ala Met Ile
145                 150                 155                 160

Asn Gly Ser Asp Gly Arg Thr Thr Val Glu Asp Leu Thr Thr Pro Pro
                165                 170                 175

Lys Trp Phe Pro Phe Pro Thr Lys Val Cys Trp Arg Lys His Asp Leu
            180                 185                 190

Ala Arg Leu Val Pro Tyr Lys Ala Pro Gly Ile Ser Asp Gly Tyr Arg
        195                 200                 205

Met Gly Met Val Leu Lys Gly Ser Asp Cys Leu Leu Ser Lys Cys Tyr
        210                 215                 220

His Glu Phe Gly Thr Gln Trp Leu Pro Leu Leu Glu Thr Leu His Gln
225                 230                 235                 240

Val Pro Val Val Pro Val Gly Leu Leu Pro Pro Glu Ile Pro Gly Asp
                245                 250                 255

Glu Lys Asp Glu Thr Trp Val Ser Ile Lys Lys Trp Leu Asp Gly Lys
            260                 265                 270

Gln Lys Gly Ser Val Val Tyr Val Ala Leu Gly Ser Glu Ala Leu Val
        275                 280                 285

Ser Gln Thr Glu Val Val Glu Leu Ala Leu Gly Leu Glu Leu Ser Gly
        290                 295                 300

Leu Pro Phe Val Trp Ala Tyr Arg Lys Pro Lys Gly Pro Ala Lys Ser
305                 310                 315                 320

Asp Ser Val Glu Leu Pro Asp Gly Phe Val Glu Arg Thr Arg Asp Arg
                325                 330                 335

Gly Leu Val Trp Thr Ser Trp Ala Pro Gln Leu Arg Ile Leu Ser His
            340                 345                 350

Glu Ser Val Cys Gly Phe Leu Thr His Cys Gly Ser Gly Ser Ile Val
        355                 360                 365

Glu Gly Leu Met Phe Gly His Pro Leu Ile Met Leu Pro Ile Phe Gly
        370                 375                 380

Asp Gln Pro Leu Asn Ala Arg Leu Leu Glu Asp Lys Gln Val Gly Ile
385                 390                 395                 400

Glu Ile Pro Arg Asn Glu Glu Asp Gly Cys Leu Thr Lys Glu Ser Val
                405                 410                 415

Ala Arg Ser Leu Arg Ser Val Val Glu Lys Glu Gly Glu Ile Tyr
            420                 425                 430

Lys Ala Asn Ala Arg Glu Leu Ser Lys Ile Tyr Asn Asp Thr Lys Val
        435                 440                 445

Glu Lys Glu Tyr Val Ser Gln Phe Val Asp Tyr Leu Glu Lys Asn Ala
        450                 455                 460

Arg Ala Val Ala Ile Asp His Glu Ser
465                 470

<210> SEQ ID NO 5
<211> LENGTH: 1422
<212> TYPE: DNA
<213> ORGANISM: Artificial Sequence
```

<220> FEATURE:
<223> OTHER INFORMATION: Synthetic oligonucleotide

<400> SEQUENCE: 5

```
atggctactt ctgattccat cgttgacgat agaaagcaat tgcatgttgc tacttttcca      60
tggttggctt tcggtcatat tttgccatac ttgcaattgt ccaagttgat tgctgaaaag     120
ggtcacaagg tttcattctt gtctaccacc agaaacatcc aaagattgtc ctctcatatc     180
tccccattga tcaacgttgt tcaattgact ttgccaagag tccaagaatt gccagaagat     240
gctgaagcta ctactgatgt tcatccagaa gatatccctt acttgaaaaa ggcttccgat     300
ggtttacaac agaagttac tagattcttg aacaacatt ccccagattg gatcatctac     360
gattatactc attactggtt gccatccatt gctgcttcat gggtatttc tagagcccat     420
ttctctgtta ctactccatg ggctattgct tatatgggtc catctgctga tgctatgatt     480
aacggttctg atggtagaac taccgttgaa gatttgacta ctccaccaaa gtggtttcca     540
tttccaacaa aagtctgttg gagaaaaaca gatttggcta gattggttcc atacaaagct     600
ccaggtattt ctgatggtta cagaatgggt atggttttga aaggttccga ttgcttgttg     660
tctaagtgct atcatgaatt cggtactcaa tggttgcctt tgttggaaac attgcatcaa     720
gttccagttg ttccagtagg tttgttgcca ccagaaattc caggtgacga aaaagacgaa     780
acttgggttt ccatcaaaaa gtggttggat ggtaagcaaa agggtctgt tgtttatgtt     840
gctttgggtt ccgaagcttt ggtttctcaa accgaagttg ttgaattggc tttgggttg     900
gaattgtctg gtttgccatt tgtttgggct tacagaaaac ctaaaggtcc agctaagtct     960
gattctgttg aattgccaga tggtttcgtt gaaagaacta gagatagagg tttggtttgg    1020
acttcttggg ctccacaatt gagaattttg tctcatgaat ccgtctgtgg tttcttgact    1080
cattgtggtt ctggttctat cgttgaaggt ttgatgtttg gtcacccatt gattatgttg    1140
ccaatctttg gtgaccaacc attgaacgct agattattgg aagataagca agtcggtatc    1200
gaaatcccaa gaaatgaaga agatggttgc ttgaccaaag aatctgttgc tagatctttg    1260
agatccgttg tcgttgaaaa agaaggtgaa atctacaagg ctaacgctag agaattgtcc    1320
aagatctaca acgataccaa ggtcgaaaaa gaatacgttt cccaattcgt tgactacttg    1380
gaaaagaatg ctagagctgt tgccattgat catgaatctt ga                        1422
```

<210> SEQ ID NO 6
<211> LENGTH: 297
<212> TYPE: PRT
<213> ORGANISM: Synechococcus sp.

<400> SEQUENCE: 6

```
Met Val Ala Gln Thr Phe Asn Leu Asp Thr Tyr Leu Ser Gln Arg Gln
1               5                   10                  15

Gln Gln Val Glu Glu Ala Leu Ser Ala Ala Leu Val Pro Ala Tyr Pro
            20                  25                  30

Glu Arg Ile Tyr Glu Ala Met Arg Tyr Ser Leu Leu Ala Gly Gly Lys
        35                  40                  45

Arg Leu Arg Pro Ile Leu Cys Leu Ala Ala Cys Glu Leu Ala Gly Gly
    50                  55                  60

Ser Val Glu Gln Ala Met Pro Thr Ala Cys Ala Leu Glu Met Ile His
65                  70                  75                  80

Thr Met Ser Leu Ile His Asp Asp Leu Pro Ala Met Asp Asn Asp Asp
                85                  90                  95
```

```
Phe Arg Arg Gly Lys Pro Thr Asn His Lys Val Phe Gly Glu Asp Ile
                100                 105                 110

Ala Ile Leu Ala Gly Asp Ala Leu Leu Ala Tyr Ala Phe Glu His Ile
            115                 120                 125

Ala Ser Gln Thr Arg Gly Val Pro Pro Gln Leu Val Leu Gln Val Ile
        130                 135                 140

Ala Arg Ile Gly His Ala Val Ala Ala Thr Gly Leu Val Gly Gly Gln
145                 150                 155                 160

Val Val Asp Leu Glu Ser Glu Gly Lys Ala Ile Ser Leu Glu Thr Leu
                165                 170                 175

Glu Tyr Ile His Ser His Lys Thr Gly Ala Leu Leu Glu Ala Ser Val
            180                 185                 190

Val Ser Gly Gly Ile Leu Ala Gly Ala Asp Glu Glu Leu Leu Ala Arg
        195                 200                 205

Leu Ser His Tyr Ala Arg Asp Ile Gly Leu Ala Phe Gln Ile Val Asp
210                 215                 220

Asp Ile Leu Asp Val Thr Ala Thr Ser Glu Gln Leu Gly Lys Thr Ala
225                 230                 235                 240

Gly Lys Asp Gln Ala Ala Ala Lys Ala Thr Tyr Pro Ser Leu Leu Gly
                245                 250                 255

Leu Glu Ala Ser Arg Gln Lys Ala Glu Glu Leu Ile Gln Ser Ala Lys
            260                 265                 270

Glu Ala Leu Arg Pro Tyr Gly Ser Gln Ala Glu Pro Leu Leu Ala Leu
        275                 280                 285

Ala Asp Phe Ile Thr Arg Arg Gln His
290                 295

<210> SEQ ID NO 7
<211> LENGTH: 827
<212> TYPE: PRT
<213> ORGANISM: Zea mays

<400> SEQUENCE: 7

Met Val Leu Ser Ser Ser Cys Thr Thr Val Pro His Leu Ser Ser Leu
1               5                   10                  15

Ala Val Val Gln Leu Gly Pro Trp Ser Ser Arg Ile Lys Lys Lys Thr
                20                  25                  30

Asp Thr Val Ala Val Pro Ala Ala Ala Gly Arg Trp Arg Arg Ala Leu
            35                  40                  45

Ala Arg Ala Gln His Thr Ser Glu Ser Ala Ala Val Ala Lys Gly Ser
        50                  55                  60

Ser Leu Thr Pro Ile Val Arg Thr Asp Ala Glu Ser Arg Arg Thr Arg
65                  70                  75                  80

Trp Pro Thr Asp Asp Asp Ala Glu Pro Leu Val Asp Glu Ile Arg
                85                  90                  95

Ala Met Leu Thr Ser Met Ser Asp Gly Asp Ile Ser Val Ser Ala Tyr
            100                 105                 110

Asp Thr Ala Trp Val Gly Leu Val Pro Arg Leu Asp Gly Gly Glu Gly
        115                 120                 125

Pro Gln Phe Pro Ala Ala Val Arg Trp Ile Arg Asn Asn Gln Leu Pro
    130                 135                 140

Asp Gly Ser Trp Gly Asp Ala Ala Leu Phe Ser Ala Tyr Asp Arg Leu
145                 150                 155                 160

Ile Asn Thr Leu Ala Cys Val Val Thr Leu Thr Arg Trp Ser Leu Glu
                165                 170                 175
```

-continued

```
Pro Glu Met Arg Gly Arg Gly Leu Ser Phe Leu Gly Arg Asn Met Trp
            180                 185                 190

Lys Leu Ala Thr Glu Asp Glu Ser Met Pro Ile Gly Phe Glu Leu
        195                 200                 205

Ala Phe Pro Ser Leu Ile Glu Leu Ala Lys Ser Leu Gly Val His Asp
    210                 215                 220

Phe Pro Tyr Asp His Gln Ala Leu Gln Gly Ile Tyr Ser Ser Arg Glu
225                 230                 235                 240

Ile Lys Met Lys Arg Ile Pro Lys Glu Val Met His Thr Val Pro Thr
                245                 250                 255

Ser Ile Leu His Ser Leu Glu Gly Met Pro Gly Leu Asp Trp Ala Lys
            260                 265                 270

Leu Leu Lys Leu Gln Ser Ser Asp Gly Ser Phe Leu Phe Ser Pro Ala
        275                 280                 285

Ala Thr Ala Tyr Ala Leu Met Asn Thr Gly Asp Asp Arg Cys Phe Ser
    290                 295                 300

Tyr Ile Asp Arg Thr Val Lys Lys Phe Asn Gly Gly Val Pro Asn Val
305                 310                 315                 320

Tyr Pro Val Asp Leu Phe Glu His Ile Trp Ala Val Asp Arg Leu Glu
                325                 330                 335

Arg Leu Gly Ile Ser Arg Tyr Phe Gln Lys Glu Ile Glu Gln Cys Met
            340                 345                 350

Asp Tyr Val Asn Arg His Trp Thr Glu Asp Gly Ile Cys Trp Ala Arg
        355                 360                 365

Asn Ser Asp Val Lys Glu Val Asp Asp Thr Ala Met Ala Phe Arg Leu
    370                 375                 380

Leu Arg Leu His Gly Tyr Ser Val Ser Pro Asp Val Phe Lys Asn Phe
385                 390                 395                 400

Glu Lys Asp Gly Glu Phe Phe Ala Phe Val Gly Gln Ser Asn Gln Ala
                405                 410                 415

Val Thr Gly Met Tyr Asn Leu Asn Arg Ala Ser Gln Ile Ser Phe Pro
            420                 425                 430

Gly Glu Asp Val Leu His Arg Ala Gly Ala Phe Ser Tyr Glu Phe Leu
        435                 440                 445

Arg Arg Lys Glu Ala Glu Gly Ala Leu Arg Asp Lys Trp Ile Ile Ser
    450                 455                 460

Lys Asp Leu Pro Gly Glu Val Val Tyr Thr Leu Asp Phe Pro Trp Tyr
465                 470                 475                 480

Gly Asn Leu Pro Arg Val Glu Ala Arg Asp Tyr Leu Glu Gln Tyr Gly
                485                 490                 495

Gly Gly Asp Asp Val Trp Ile Gly Lys Thr Leu Tyr Arg Met Pro Leu
            500                 505                 510

Val Asn Asn Asp Val Tyr Leu Glu Leu Ala Arg Met Asp Phe Asn His
        515                 520                 525

Cys Gln Ala Leu His Gln Leu Glu Trp Gln Gly Leu Lys Arg Trp Tyr
    530                 535                 540

Thr Glu Asn Arg Leu Met Asp Phe Gly Val Ala Gln Glu Asp Ala Leu
545                 550                 555                 560

Arg Ala Tyr Phe Leu Ala Ala Ala Ser Val Tyr Glu Pro Cys Arg Ala
                565                 570                 575

Ala Glu Arg Leu Ala Trp Ala Arg Ala Ala Ile Leu Ala Asn Ala Val
            580                 585                 590
```

```
Ser Thr His Leu Arg Asn Ser Pro Ser Phe Arg Glu Arg Leu Glu His
        595                 600                 605

Ser Leu Arg Cys Arg Pro Ser Glu Glu Thr Asp Gly Ser Trp Phe Asn
610                 615                 620

Ser Ser Ser Gly Ser Asp Ala Val Leu Val Lys Ala Val Leu Arg Leu
625                 630                 635                 640

Thr Asp Ser Leu Ala Arg Glu Ala Gln Pro Ile His Gly Gly Asp Pro
            645                 650                 655

Glu Asp Ile Ile His Lys Leu Leu Arg Ser Ala Trp Ala Glu Trp Val
                660                 665                 670

Arg Glu Lys Ala Asp Ala Ala Asp Ser Val Cys Asn Gly Ser Ser Ala
            675                 680                 685

Val Glu Gln Glu Gly Ser Arg Met Val His Asp Lys Gln Thr Cys Leu
690                 695                 700

Leu Leu Ala Arg Met Ile Glu Ile Ser Ala Gly Arg Ala Ala Gly Glu
705                 710                 715                 720

Ala Ala Ser Glu Asp Gly Asp Arg Arg Ile Ile Gln Leu Thr Gly Ser
            725                 730                 735

Ile Cys Asp Ser Leu Lys Gln Lys Met Leu Val Ser Gln Asp Pro Glu
                740                 745                 750

Lys Asn Glu Glu Met Met Ser His Val Asp Asp Glu Leu Lys Leu Arg
            755                 760                 765

Ile Arg Glu Phe Val Gln Tyr Leu Leu Arg Leu Gly Glu Lys Lys Thr
770                 775                 780

Gly Ser Ser Glu Thr Arg Gln Thr Phe Leu Ser Ile Val Lys Ser Cys
785                 790                 795                 800

Tyr Tyr Ala Ala His Cys Pro Pro His Val Val Asp Arg His Ile Ser
            805                 810                 815

Arg Val Ile Phe Glu Pro Val Ser Ala Ala Lys
                820                 825

<210> SEQ ID NO 8
<211> LENGTH: 785
<212> TYPE: PRT
<213> ORGANISM: Arabidopsis thaliana

<400> SEQUENCE: 8

Met Ser Ile Asn Leu Arg Ser Ser Gly Cys Ser Ser Pro Ile Ser Ala
1               5                   10                  15

Thr Leu Glu Arg Gly Leu Asp Ser Glu Val Gln Thr Arg Ala Asn Asn
            20                  25                  30

Val Ser Phe Glu Gln Thr Lys Glu Lys Ile Arg Lys Met Leu Glu Lys
        35                  40                  45

Val Glu Leu Ser Val Ser Ala Tyr Asp Thr Ser Trp Val Ala Met Val
    50                  55                  60

Pro Ser Pro Ser Ser Gln Asn Ala Pro Leu Phe Pro Gln Cys Val Lys
65                  70                  75                  80

Trp Leu Leu Asp Asn Gln His Glu Asp Gly Ser Trp Gly Leu Asp Asn
                85                  90                  95

His Asp His Gln Ser Leu Lys Lys Asp Val Leu Ser Ser Thr Leu Ala
            100                 105                 110

Ser Ile Leu Ala Leu Lys Lys Trp Gly Ile Gly Glu Arg Gln Ile Asn
        115                 120                 125

Lys Gly Leu Gln Phe Ile Glu Leu Asn Ser Ala Leu Val Thr Asp Glu
    130                 135                 140
```

-continued

```
Thr Ile Gln Lys Pro Thr Gly Phe Asp Ile Ile Phe Pro Gly Met Ile
145                 150                 155                 160

Lys Tyr Ala Arg Asp Leu Asn Leu Thr Ile Pro Leu Gly Ser Glu Val
            165                 170                 175

Val Asp Asp Met Ile Arg Lys Arg Asp Leu Asp Leu Lys Cys Asp Ser
        180                 185                 190

Glu Lys Phe Ser Lys Gly Arg Glu Ala Tyr Leu Ala Tyr Val Leu Glu
    195                 200                 205

Gly Thr Arg Asn Leu Lys Asp Trp Asp Leu Ile Val Lys Tyr Gln Arg
210                 215                 220

Lys Asn Gly Ser Leu Phe Asp Ser Pro Ala Thr Ala Ala Ala Phe
225                 230                 235                 240

Thr Gln Phe Gly Asn Asp Gly Cys Leu Arg Tyr Leu Cys Ser Leu Leu
                245                 250                 255

Gln Lys Phe Glu Ala Ala Val Pro Ser Val Tyr Pro Phe Asp Gln Tyr
            260                 265                 270

Ala Arg Leu Ser Ile Ile Val Thr Leu Glu Ser Leu Gly Ile Asp Arg
        275                 280                 285

Asp Phe Lys Thr Glu Ile Lys Ser Ile Leu Asp Glu Thr Tyr Arg Tyr
    290                 295                 300

Trp Leu Arg Gly Asp Glu Glu Ile Cys Leu Asp Leu Ala Thr Cys Ala
305                 310                 315                 320

Leu Ala Phe Arg Leu Leu Leu Ala His Gly Tyr Asp Val Ser Tyr Asp
                325                 330                 335

Pro Leu Lys Pro Phe Ala Glu Glu Ser Gly Phe Ser Asp Thr Leu Glu
            340                 345                 350

Gly Tyr Val Lys Asn Thr Phe Ser Val Leu Glu Leu Phe Lys Ala Ala
        355                 360                 365

Gln Ser Tyr Pro His Glu Ser Ala Leu Lys Lys Gln Cys Cys Trp Thr
    370                 375                 380

Lys Gln Tyr Leu Glu Met Glu Leu Ser Ser Trp Val Lys Thr Ser Val
385                 390                 395                 400

Arg Asp Lys Tyr Leu Lys Lys Glu Val Glu Asp Ala Leu Ala Phe Pro
                405                 410                 415

Ser Tyr Ala Ser Leu Glu Arg Ser Asp His Arg Arg Lys Ile Leu Asn
            420                 425                 430

Gly Ser Ala Val Glu Asn Thr Arg Val Thr Lys Thr Ser Tyr Arg Leu
        435                 440                 445

His Asn Ile Cys Thr Ser Asp Ile Leu Lys Leu Ala Val Asp Asp Phe
    450                 455                 460

Asn Phe Cys Gln Ser Ile His Arg Glu Glu Met Glu Arg Leu Asp Arg
465                 470                 475                 480

Trp Ile Val Glu Asn Arg Leu Gln Glu Leu Lys Phe Ala Arg Gln Lys
                485                 490                 495

Leu Ala Tyr Cys Tyr Phe Ser Gly Ala Ala Thr Leu Phe Ser Pro Glu
            500                 505                 510

Leu Ser Asp Ala Arg Ile Ser Trp Ala Lys Gly Gly Val Leu Thr Thr
        515                 520                 525

Val Val Asp Asp Phe Phe Asp Val Gly Gly Ser Lys Glu Glu Leu Glu
    530                 535                 540

Asn Leu Ile His Leu Val Glu Lys Trp Asp Leu Asn Gly Val Pro Glu
545                 550                 555                 560
```

```
Tyr Ser Ser Glu His Val Glu Ile Ile Phe Ser Val Leu Arg Asp Thr
            565                 570                 575
Ile Leu Glu Thr Gly Asp Lys Ala Phe Thr Tyr Gln Gly Arg Asn Val
        580                 585                 590
Thr His His Ile Val Lys Ile Trp Leu Asp Leu Leu Lys Ser Met Leu
    595                 600                 605
Arg Glu Ala Glu Trp Ser Ser Asp Lys Ser Thr Pro Ser Leu Glu Asp
610                 615                 620
Tyr Met Glu Asn Ala Tyr Ile Ser Phe Ala Leu Gly Pro Ile Val Leu
625                 630                 635                 640
Pro Ala Thr Tyr Leu Ile Gly Pro Pro Leu Pro Glu Lys Thr Val Asp
            645                 650                 655
Ser His Gln Tyr Asn Gln Leu Tyr Lys Leu Val Ser Thr Met Gly Arg
        660                 665                 670
Leu Leu Asn Asp Ile Gln Gly Phe Lys Arg Glu Ser Ala Glu Gly Lys
    675                 680                 685
Leu Asn Ala Val Ser Leu His Met Lys His Glu Arg Asp Asn Arg Ser
690                 695                 700
Lys Glu Val Ile Ile Glu Ser Met Lys Gly Leu Ala Glu Arg Lys Arg
705                 710                 715                 720
Glu Glu Leu His Lys Leu Val Leu Glu Glu Lys Gly Ser Val Val Pro
            725                 730                 735
Arg Glu Cys Lys Glu Ala Phe Leu Lys Met Ser Lys Val Leu Asn Leu
        740                 745                 750
Phe Tyr Arg Lys Asp Asp Gly Phe Thr Ser Asn Asp Leu Met Ser Leu
    755                 760                 765
Val Lys Ser Val Ile Tyr Glu Pro Val Ser Leu Gln Lys Glu Ser Leu
770                 775                 780
Thr
785

<210> SEQ ID NO 9
<211> LENGTH: 1542
<212> TYPE: DNA
<213> ORGANISM: Artificial Sequence
<220> FEATURE:
<223> OTHER INFORMATION: Codon-optimized KO

<400> SEQUENCE: 9
atggatgctg tgacgggttt gttaactgtc ccagcaaccg ctataactat tggtggaact    60
gctgtagcat tggcggtagc gctaatcttt tggtacctga atcctacac atcagctaga   120
agatcccaat caaatcatct tccaagagtg cctgaagtcc aggtgttcc attgttagga   180
aatctgttac aattgaagga gaaaaagcca tacatgactt ttacgagatg ggcagcgaca   240
tatggaccta tctatagtat caaaactggg gctacaagta tggttgtggt atcatctaat   300
gagatagcca aggaggcatt ggtgaccaga ttccaatcca tatctacaag gaacttatct   360
aaagccctga agtacttac agcagataag acaatggtcg caatgtcaga ttatgatgat   420
tatcataaaa cagttaagag acacatactg accgccgtct gggtcctaa tgcacagaaa   480
agcatagaa ttcacagaga tatcatgatg gataacatat ctactcaact tcatgaattc   540
gtgaaaaaca acccagaaca ggaagaggta gaccttagaa aaatctttca atctgagtta   600
ttcggcttag ctatgagaca agccttagga aaggatgttg aaagtttgta cgttgaagac   660
ctgaaaatca ctatgaatag agacgaaatc tttcaagtcc ttgttgttga tccaatgatg   720
```

-continued

```
ggagcaatcg atgttgattg gagagacttc tttccatacc taaagtgggt cccaaacaaa    780
aagttcgaaa atactattca acaaatgtac atcagaagag aagctgttat gaaatcttta    840
atcaaagagc acaaaaagag aatagcgtca ggcgaaaagc taaatagtta tatcgattac    900
cttttatctg aagctcaaac tttaaccgat cagcaactat tgatgtcctt gtgggaacca    960
atcattgaat cttcagatac aacaatggtc acaacagaat gggcaatgta cgaattagct   1020
aaaaaccta aattgcaaga taggttgtac agagacatta agtccgtctg tggatctgaa   1080
aagataaccg aagagcatct atcacagctg ccttacatta cagctatttt ccacgaaaca   1140
ctgagaagac actcaccagt tcctatcatt cctctaagac atgtacatga agataccgtt   1200
ctaggcggct accatgttcc tgctggcaca gaacttgccg ttaacatcta cggttgcaac   1260
atggacaaaa acgtttggga aaatccagag gaatggaacc cagaaagatt catgaaagag   1320
aatgagacaa ttgattttca aaagacgatg gccttcggtg gtggtaagag agtttgtgct   1380
ggttccttgc aagccctttt aactgcatct attgggattg ggagaatggt tcaagagttc   1440
gaatggaaac tgaaggatat gactcaagag gaagtgaaca cgataggcct aactacacaa   1500
atgttaagac cattgagagc tattatcaaa cctaggatct aa                      1542
```

<210> SEQ ID NO 10
<211> LENGTH: 513
<212> TYPE: PRT
<213> ORGANISM: Stevia rebaudiana

<400> SEQUENCE: 10

```
Met Asp Ala Val Thr Gly Leu Leu Thr Val Pro Ala Thr Ala Ile Thr
1               5                   10                  15

Ile Gly Gly Thr Ala Val Ala Leu Ala Val Ala Leu Ile Phe Trp Tyr
            20                  25                  30

Leu Lys Ser Tyr Thr Ser Ala Arg Arg Ser Gln Ser Asn His Leu Pro
        35                  40                  45

Arg Val Pro Glu Val Pro Gly Val Pro Leu Leu Gly Asn Leu Leu Gln
    50                  55                  60

Leu Lys Glu Lys Lys Pro Tyr Met Thr Phe Thr Arg Trp Ala Ala Thr
65                  70                  75                  80

Tyr Gly Pro Ile Tyr Ser Ile Lys Thr Gly Ala Thr Ser Met Val Val
                85                  90                  95

Val Ser Ser Asn Glu Ile Ala Lys Glu Ala Leu Val Thr Arg Phe Gln
            100                 105                 110

Ser Ile Ser Thr Arg Asn Leu Ser Lys Ala Leu Lys Val Leu Thr Ala
        115                 120                 125

Asp Lys Thr Met Val Ala Met Ser Asp Tyr Asp Asp Tyr His Lys Thr
    130                 135                 140

Val Lys Arg His Ile Leu Thr Ala Val Leu Gly Pro Asn Ala Gln Lys
145                 150                 155                 160

Lys His Arg Ile His Arg Asp Ile Met Met Asp Asn Ile Ser Thr Gln
                165                 170                 175

Leu His Glu Phe Val Lys Asn Asn Pro Glu Gln Glu Glu Val Asp Leu
            180                 185                 190

Arg Lys Ile Phe Gln Ser Glu Leu Phe Gly Leu Ala Met Arg Gln Ala
        195                 200                 205

Leu Gly Lys Asp Val Glu Ser Leu Tyr Val Glu Asp Leu Lys Ile Thr
    210                 215                 220

Met Asn Arg Asp Glu Ile Phe Gln Val Leu Val Val Asp Pro Met Met
```

```
              225                 230                 235                 240
        Gly Ala Ile Asp Val Asp Trp Arg Asp Phe Phe Pro Tyr Leu Lys Trp
                        245                 250                 255

Val Pro Asn Lys Lys Phe Glu Asn Thr Ile Gln Gln Met Tyr Ile Arg
                        260                 265                 270

Arg Glu Ala Val Met Lys Ser Leu Ile Lys Glu His Lys Lys Arg Ile
                    275                 280                 285

Ala Ser Gly Glu Lys Leu Asn Ser Tyr Ile Asp Tyr Leu Leu Ser Glu
                290                 295                 300

Ala Gln Thr Leu Thr Asp Gln Gln Leu Leu Met Ser Leu Trp Glu Pro
        305                 310                 315                 320

Ile Ile Glu Ser Ser Asp Thr Thr Met Val Thr Thr Glu Trp Ala Met
                        325                 330                 335

Tyr Glu Leu Ala Lys Asn Pro Lys Leu Gln Asp Arg Leu Tyr Arg Asp
                        340                 345                 350

Ile Lys Ser Val Cys Gly Ser Glu Lys Ile Thr Glu Glu His Leu Ser
                    355                 360                 365

Gln Leu Pro Tyr Ile Thr Ala Ile Phe His Glu Thr Leu Arg Arg His
                370                 375                 380

Ser Pro Val Pro Ile Ile Pro Leu Arg His Val His Glu Asp Thr Val
        385                 390                 395                 400

Leu Gly Gly Tyr His Val Pro Ala Gly Thr Glu Leu Ala Val Asn Ile
                        405                 410                 415

Tyr Gly Cys Asn Met Asp Lys Asn Val Trp Glu Asn Pro Glu Glu Trp
                        420                 425                 430

Asn Pro Glu Arg Phe Met Lys Glu Asn Glu Thr Ile Asp Phe Gln Lys
                    435                 440                 445

Thr Met Ala Phe Gly Gly Gly Lys Arg Val Cys Ala Gly Ser Leu Gln
                450                 455                 460

Ala Leu Leu Thr Ala Ser Ile Gly Ile Gly Arg Met Val Gln Glu Phe
        465                 470                 475                 480

Glu Trp Lys Leu Lys Asp Met Thr Gln Glu Glu Val Asn Thr Ile Gly
                        485                 490                 495

Leu Thr Thr Gln Met Leu Arg Pro Leu Arg Ala Ile Ile Lys Pro Arg
                        500                 505                 510

Ile

<210> SEQ ID NO 11
<211> LENGTH: 2139
<212> TYPE: DNA
<213> ORGANISM: Arabidopsis thaliana

<400> SEQUENCE: 11
atgtcttcct cttcctcttc cagtacctct atgattgatt tgatggctgc tattattaaa    60
ggtgaaccag ttatcgtctc cgacccagca aatgcctctg cttatgaatc agttgctgca   120
gaattgtctt caatgttgat cgaaaacaga caattcgcca tgatcgtaac tacatcaatc   180
gctgttttga tcggttgtat tgtcatgttg gtatggagaa gatccggtag tggtaattct   240
aaaagagtcg aacctttgaa accattagta attaagccaa gagaagaaga aatagatgac   300
ggtagaaaga agttacaat attttttcggt acccaaactg gtacagctga aggttttgca   360
aaagccttag gtgaagaagc taaggcaaga tacgaaaaga ctagattcaa gatagtcgat   420
ttggatgact atgccgctga tgacgatgaa tacgaagaaa agttgaagaa agaagatgtt   480
```

-continued

```
gcatttttct tttggcaac ctatggtgac ggtgaaccaa ctgacaatgc agccagattc    540
tacaaatggt ttacagaggg taatgatcgt ggtgaatggt tgaaaaactt aaagtacggt    600
gttttcggtt tgggtaacag acaatacgaa catttcaaca aagttgcaaa ggttgtcgac    660
gatattttgg tcgaacaagg tgctcaaaga ttagtccaag taggtttggg tgacgatgac    720
caatgtatag aagatgactt tactgcctgg agagaagctt tgtggcctga attagacaca    780
atcttgagag aagaaggtga caccgccgtt gctaccccat atactgctgc agtattagaa    840
tacagagttt ccatccatga tagtgaagac gcaaagttta atgatatcac tttggccaat    900
ggtaacggtt atacagtttt cgatgcacaa cacccttaca aagctaacgt tgcagtcaag    960
agagaattac atacaccaga atccgacaga agttgtatac acttggaatt tgatatcgct   1020
ggttccggtt taaccatgaa gttgggtgac catgtaggtg ttttatgcga caatttgtct   1080
gaaactgttg atgaagcatt gagattgttg gatatgtccc ctgacactta ttttagtttg   1140
cacgctgaaa aagaagatgg tacaccaatt tccagttctt taccacctcc attccctcca   1200
tgtaacttaa gaacagcctt gaccagatac gcttgcttgt tatcatcccc taaaaagtcc   1260
gccttggttg ctttagccgc tcatgctagt gatcctactg aagcagaaag attgaaacac   1320
ttagcatctc cagccggtaa agatgaatat tcaaagtggg tagttgaatc tcaaagatca   1380
ttgttagaag ttatggcaga atttccatct gccaagcctc cattaggtgt cttctttgct   1440
ggtgtagcac ctagattgca accaagattc tactcaatca gttcttcacc taagatcgct   1500
gaaactagaa ttcatgttac atgtgcatta gtctacgaaa agatgccaac cggtagaatt   1560
cacaagggtg tatgctctac ttggatgaaa aatgctgttc cttacgaaaa atcagaaaag   1620
ttgttcttag gtagaccaat cttcgtaaga caatcaaact tcaagttgcc ttctgattca   1680
aaggttccaa taatcatgat aggtcctggt acaggtttag ccccattcag aggtttcttg   1740
caagaaagat tggctttagt tgaatctggt gtcgaattag gtccttcagt tttgttcttt   1800
ggttgtagaa acagaagaat ggatttcatc tatgaagaag aattgcaaag attcgtcgaa   1860
tctggtgcat tggccgaatt atctgtagct tttcaagag aaggtccaac taaggaatac   1920
gttcaacata agatgatgga taaggcatcc gacatatgga acatgatcag tcaaggtgct   1980
tatttgtacg tttgcggtga cgcaaagggt atggccagag atgtccatag atctttgcac   2040
acaattgctc aagaacaagg ttccatggat agtaccaaag ctgaaggttt cgtaaagaac   2100
ttacaaactt ccggtagata cttgagagat gtctggtga                          2139
```

<210> SEQ ID NO 12
<211> LENGTH: 712
<212> TYPE: PRT
<213> ORGANISM: Arabidopsis thaliana

<400> SEQUENCE: 12

```
Met Ser Ser Ser Ser Ser Ser Ser Thr Ser Met Ile Asp Leu Met Ala
1               5                   10                  15

Ala Ile Ile Lys Gly Glu Pro Val Ile Val Ser Asp Pro Ala Asn Ala
            20                  25                  30

Ser Ala Tyr Glu Ser Val Ala Ala Glu Leu Ser Ser Met Leu Ile Glu
        35                  40                  45

Asn Arg Gln Phe Ala Met Ile Val Thr Thr Ser Ile Ala Val Leu Ile
    50                  55                  60

Gly Cys Ile Val Met Leu Val Trp Arg Arg Ser Gly Ser Gly Asn Ser
65                  70                  75                  80
```

-continued

```
Lys Arg Val Glu Pro Leu Lys Pro Leu Val Ile Lys Pro Arg Glu Glu
                 85                  90                  95
Glu Ile Asp Asp Gly Arg Lys Lys Val Thr Ile Phe Phe Gly Thr Gln
            100                 105                 110
Thr Gly Thr Ala Glu Gly Phe Ala Lys Ala Leu Gly Glu Glu Ala Lys
        115                 120                 125
Ala Arg Tyr Glu Lys Thr Arg Phe Lys Ile Val Asp Leu Asp Asp Tyr
    130                 135                 140
Ala Ala Asp Asp Asp Glu Tyr Glu Glu Lys Leu Lys Lys Glu Asp Val
145                 150                 155                 160
Ala Phe Phe Phe Leu Ala Thr Tyr Gly Asp Gly Glu Pro Thr Asp Asn
                165                 170                 175
Ala Ala Arg Phe Tyr Lys Trp Phe Thr Glu Gly Asn Asp Arg Gly Glu
            180                 185                 190
Trp Leu Lys Asn Leu Lys Tyr Gly Val Phe Gly Leu Gly Asn Arg Gln
        195                 200                 205
Tyr Glu His Phe Asn Lys Val Ala Lys Val Val Asp Asp Ile Leu Val
    210                 215                 220
Glu Gln Gly Ala Gln Arg Leu Val Gln Val Gly Leu Gly Asp Asp Asp
225                 230                 235                 240
Gln Cys Ile Glu Asp Asp Phe Thr Ala Trp Arg Glu Ala Leu Trp Pro
                245                 250                 255
Glu Leu Asp Thr Ile Leu Arg Glu Glu Gly Asp Thr Ala Val Ala Thr
            260                 265                 270
Pro Tyr Thr Ala Ala Val Leu Glu Tyr Arg Val Ser Ile His Asp Ser
        275                 280                 285
Glu Asp Ala Lys Phe Asn Asp Ile Thr Leu Ala Asn Gly Asn Gly Tyr
    290                 295                 300
Thr Val Phe Asp Ala Gln His Pro Tyr Lys Ala Asn Val Ala Val Lys
305                 310                 315                 320
Arg Glu Leu His Thr Pro Glu Ser Asp Arg Ser Cys Ile His Leu Glu
                325                 330                 335
Phe Asp Ile Ala Gly Ser Gly Leu Thr Met Lys Leu Gly Asp His Val
            340                 345                 350
Gly Val Leu Cys Asp Asn Leu Ser Glu Thr Val Asp Glu Ala Leu Arg
        355                 360                 365
Leu Leu Asp Met Ser Pro Asp Thr Tyr Phe Ser Leu His Ala Glu Lys
    370                 375                 380
Glu Asp Gly Thr Pro Ile Ser Ser Ser Leu Pro Pro Pro Phe Pro Pro
385                 390                 395                 400
Cys Asn Leu Arg Thr Ala Leu Thr Arg Tyr Ala Cys Leu Leu Ser Ser
                405                 410                 415
Pro Lys Lys Ser Ala Leu Val Ala Leu Ala Ala His Ala Ser Asp Pro
            420                 425                 430
Thr Glu Ala Glu Arg Leu Lys His Leu Ala Ser Pro Ala Gly Lys Asp
        435                 440                 445
Glu Tyr Ser Lys Trp Val Val Glu Ser Gln Arg Ser Leu Leu Glu Val
    450                 455                 460
Met Ala Glu Phe Pro Ser Ala Lys Pro Pro Leu Gly Val Phe Phe Ala
465                 470                 475                 480
Gly Val Ala Pro Arg Leu Gln Pro Arg Phe Tyr Ser Ile Ser Ser Ser
                485                 490                 495
Pro Lys Ile Ala Glu Thr Arg Ile His Val Thr Cys Ala Leu Val Tyr
```

```
                    500                 505                 510
Glu Lys Met Pro Thr Gly Arg Ile His Lys Gly Val Cys Ser Thr Trp
            515                 520                 525

Met Lys Asn Ala Val Pro Tyr Glu Lys Ser Glu Lys Leu Phe Leu Gly
        530                 535                 540

Arg Pro Ile Phe Val Arg Gln Ser Asn Phe Lys Leu Pro Ser Asp Ser
545                 550                 555                 560

Lys Val Pro Ile Ile Met Ile Gly Pro Thr Gly Leu Ala Pro Phe
                565                 570                 575

Arg Gly Phe Leu Gln Glu Arg Leu Ala Leu Val Glu Ser Gly Val Glu
            580                 585                 590

Leu Gly Pro Ser Val Leu Phe Phe Gly Cys Arg Asn Arg Arg Met Asp
        595                 600                 605

Phe Ile Tyr Glu Glu Glu Leu Gln Arg Phe Val Glu Ser Gly Ala Leu
    610                 615                 620

Ala Glu Leu Ser Val Ala Phe Ser Arg Glu Gly Pro Thr Lys Glu Tyr
625                 630                 635                 640

Val Gln His Lys Met Met Asp Lys Ala Ser Asp Ile Trp Asn Met Ile
                645                 650                 655

Ser Gln Gly Ala Tyr Leu Tyr Val Cys Gly Asp Ala Lys Gly Met Ala
            660                 665                 670

Arg Asp Val His Arg Ser Leu His Thr Ile Ala Gln Glu Gln Gly Ser
        675                 680                 685

Met Asp Ser Thr Lys Ala Glu Gly Phe Val Lys Asn Leu Gln Thr Ser
    690                 695                 700

Gly Arg Tyr Leu Arg Asp Val Trp
705                 710

<210> SEQ ID NO 13
<211> LENGTH: 462
<212> TYPE: PRT
<213> ORGANISM: Oryza sativa

<400> SEQUENCE: 13

Met Asp Ser Gly Tyr Ser Ser Ser Tyr Ala Ala Ala Gly Met His
1               5                   10                  15

Val Val Ile Cys Pro Trp Leu Ala Phe Gly His Leu Leu Pro Cys Leu
            20                  25                  30

Asp Leu Ala Gln Arg Leu Ala Ser Arg Gly His Arg Val Ser Phe Val
        35                  40                  45

Ser Thr Pro Arg Asn Ile Ser Arg Leu Pro Pro Val Arg Pro Ala Leu
    50                  55                  60

Ala Pro Leu Val Ala Phe Val Ala Leu Pro Leu Pro Arg Val Glu Gly
65                  70                  75                  80

Leu Pro Asp Gly Ala Glu Ser Thr Asn Asp Val Pro His Asp Arg Pro
                85                  90                  95

Asp Met Val Glu Leu His Arg Arg Ala Phe Asp Gly Leu Ala Ala Pro
            100                 105                 110

Phe Ser Glu Phe Leu Gly Thr Ala Cys Ala Asp Trp Val Ile Val Asp
        115                 120                 125

Val Phe His His Trp Ala Ala Ala Ala Leu Glu His Lys Val Pro
    130                 135                 140

Cys Ala Met Met Leu Leu Gly Ser Ala His Met Ile Ala Ser Ile Ala
145                 150                 155                 160
```

Asp Arg Arg Leu Glu Arg Ala Glu Thr Glu Ser Pro Ala Ala Ala Gly
            165                 170                 175

Gln Gly Arg Pro Ala Ala Ala Pro Thr Phe Glu Val Ala Arg Met Lys
        180                 185                 190

Leu Ile Arg Thr Lys Gly Ser Ser Gly Met Ser Leu Ala Glu Arg Phe
    195                 200                 205

Ser Leu Thr Leu Ser Arg Ser Ser Leu Val Val Gly Arg Ser Cys Val
210                 215                 220

Glu Phe Glu Pro Glu Thr Val Pro Leu Leu Ser Thr Leu Arg Gly Lys
225                 230                 235                 240

Pro Ile Thr Phe Leu Gly Leu Met Pro Pro Leu His Glu Gly Arg Arg
            245                 250                 255

Glu Asp Gly Glu Asp Ala Thr Val Arg Trp Leu Asp Ala Gln Pro Ala
        260                 265                 270

Lys Ser Val Val Tyr Val Ala Leu Gly Ser Glu Val Pro Leu Gly Val
    275                 280                 285

Glu Lys Val His Glu Leu Ala Leu Gly Leu Glu Leu Ala Gly Thr Arg
290                 295                 300

Phe Leu Trp Ala Leu Arg Lys Pro Thr Gly Val Ser Asp Ala Asp Leu
305                 310                 315                 320

Leu Pro Ala Gly Phe Glu Glu Arg Thr Arg Gly Arg Gly Val Val Ala
            325                 330                 335

Thr Arg Trp Val Pro Gln Met Ser Ile Leu Ala His Ala Ala Val Gly
        340                 345                 350

Ala Phe Leu Thr His Cys Gly Trp Asn Ser Thr Ile Glu Gly Leu Met
    355                 360                 365

Phe Gly His Pro Leu Ile Met Leu Pro Ile Phe Gly Asp Gln Gly Pro
370                 375                 380

Asn Ala Arg Leu Ile Glu Ala Lys Asn Ala Gly Leu Gln Val Ala Arg
385                 390                 395                 400

Asn Asp Gly Asp Gly Ser Phe Asp Arg Glu Gly Val Ala Ala Ala Ile
            405                 410                 415

Arg Ala Val Ala Val Glu Glu Glu Ser Ser Lys Val Phe Gln Ala Lys
        420                 425                 430

Ala Lys Lys Leu Gln Glu Ile Val Ala Asp Met Ala Cys His Glu Arg
    435                 440                 445

Tyr Ile Asp Gly Phe Ile Gln Gln Leu Arg Ser Tyr Lys Asp
450                 455                 460

<210> SEQ ID NO 14
<211> LENGTH: 1503
<212> TYPE: DNA
<213> ORGANISM: Artificial Sequence
<220> FEATURE:
<223> OTHER INFORMATION: Codon-optimized stevia rebaudiana

<400> SEQUENCE: 14
atggaagcct cttacctata catttctatt ttgcttttac tggcatcata cctgttcacc      60
actcaactta gaaggaagag cgctaatcta ccaccaaccg tgtttccatc aataccaatc     120
attggacact atacttact caaaaagcct ctttatagaa ctttagcaaa aattgccgct     180
aagtacggac caatactgca attacaactc ggctacagac gtgttctggt gatttcctca     240
ccatcagcag cagaagagtg ctttaccaat aacgatgtaa tcttcgcaaa tagacctaag     300
acattgtttg gcaaaatagt gggtggaaca tcccttggca gttatcctat cggcgatcaa     360

```
tggcgtaatc taaggagagt agcttctatc gaaatcctat cagttcatag gttgaacgaa    420
tttcatgata tcagagtgga tgagaacaga ttgttaatta gaaaacttag aagttcatct    480
tctcctgtta ctcttataac agtctttat gctctaacat tgaacgtcat tatgagaatg    540
atctctggca aaagatattt cgacagtggg gatagagaat ggaggagga aggtaagaga    600 tttcgagaaa tcttagacga aacgttgctt ctagccggtg cttctaatgt tggcgactac    660
ttaccaatat tgaactggtt gggagttaag tctcttgaaa agaaattgat cgctttgcag    720 aaaagagag atgacttttt ccagggtttg attgaacagg ttagaaaatc tcgtggtgct    780
aaagtaggca aagtagaaa aacgatgatc gaactcttat tatctttgca agagtcagaa    840
cctgagtact atacagatgc tatgataaga tcttttgtcc taggtctgct ggctgcaggt    900
agtgatactt cagcgggcac tatggaatgg gccatgagct tactggtcaa tcacccacat    960
gtattgaaga aagctcaagc tgaaatcgat agagttatcg gtaataacag attgattgac   1020
gagtcagaca ttggaaatat cccttacatc gggtgtatta tcaatgaaac tctaagactc   1080
tatccagcag ggccattgtt gttcccacat gaaagttctg ccgactgcgt tatttccggt   1140
tacaatatac ctagaggtac aatgttaatc gtaaaccaat gggcgattca tcacgatcct   1200
aaagtctggg atgatcctga aacctttaaa cctgaaagat ttcaaggatt agaaggaact   1260
agagatggtt tcaaacttat gccattcggt tctgggagaa gaggatgtcc aggtgaaggt   1320
ttggcaataa ggctgttagg gatgacacta ggctcagtga tccaatgttt tgattgggag   1380
agagtaggag atgagatggt tgacatgaca gaaggtttgg gtgtcacact tcctaaggcc   1440
gttccattag ttgccaaatg taagccacgt tccgaaatga ctaatctcct atccgaactt   1500
taa                                                                1503

<210> SEQ ID NO 15
<211> LENGTH: 500
<212> TYPE: PRT
<213> ORGANISM: Stevia rebaudiana

<400> SEQUENCE: 15

Met Glu Ala Ser Tyr Leu Tyr Ile Ser Ile Leu Leu Leu Ala Ser
1               5                   10                  15

Tyr Leu Phe Thr Thr Gln Leu Arg Arg Lys Ser Ala Asn Leu Pro Pro
            20                  25                  30

Thr Val Phe Pro Ser Ile Pro Ile Gly His Leu Tyr Leu Leu Lys
        35                  40                  45

Lys Pro Leu Tyr Arg Thr Leu Ala Lys Ile Ala Ala Lys Tyr Gly Pro
    50                  55                  60

Ile Leu Gln Leu Gln Leu Gly Tyr Arg Arg Val Leu Val Ile Ser Ser
65                  70                  75                  80

Pro Ser Ala Ala Glu Glu Cys Phe Thr Asn Asn Asp Val Ile Phe Ala
                85                  90                  95

Asn Arg Pro Lys Thr Leu Phe Gly Lys Ile Val Gly Gly Thr Ser Leu
            100                 105                 110

Gly Ser Leu Ser Tyr Gly Asp Gln Trp Arg Asn Leu Arg Arg Val Ala
        115                 120                 125

Ser Ile Glu Ile Leu Ser Val His Arg Leu Asn Glu Phe His Asp Ile
    130                 135                 140

Arg Val Asp Glu Asn Arg Leu Leu Ile Arg Lys Leu Arg Ser Ser Ser
145                 150                 155                 160

Ser Pro Val Thr Leu Ile Thr Val Phe Tyr Ala Leu Thr Leu Asn Val
```

```
                    165                 170                 175
Ile Met Arg Met Ile Ser Gly Lys Arg Tyr Phe Asp Ser Gly Asp Arg
            180                 185                 190

Glu Leu Glu Glu Gly Lys Arg Phe Arg Glu Ile Leu Asp Glu Thr
    195                 200                 205

Leu Leu Leu Ala Gly Ala Ser Asn Val Gly Asp Tyr Leu Pro Ile Leu
        210                 215                 220

Asn Trp Leu Gly Val Lys Ser Leu Glu Lys Lys Leu Ile Ala Leu Gln
225                 230                 235                 240

Lys Lys Arg Asp Asp Phe Phe Gln Gly Leu Ile Glu Gln Val Arg Lys
                245                 250                 255

Ser Arg Gly Ala Lys Val Gly Lys Gly Arg Lys Thr Met Ile Glu Leu
            260                 265                 270

Leu Leu Ser Leu Gln Glu Ser Glu Pro Glu Tyr Tyr Thr Asp Ala Met
        275                 280                 285

Ile Arg Ser Phe Val Leu Gly Leu Leu Ala Ala Gly Ser Asp Thr Ser
    290                 295                 300

Ala Gly Thr Met Glu Trp Ala Met Ser Leu Leu Val Asn His Pro His
305                 310                 315                 320

Val Leu Lys Lys Ala Gln Ala Glu Ile Asp Arg Val Ile Gly Asn Asn
                325                 330                 335

Arg Leu Ile Asp Glu Ser Asp Ile Gly Asn Ile Pro Tyr Ile Gly Cys
            340                 345                 350

Ile Ile Asn Glu Thr Leu Arg Leu Tyr Pro Ala Gly Pro Leu Leu Phe
        355                 360                 365

Pro His Glu Ser Ser Ala Asp Cys Val Ile Ser Gly Tyr Asn Ile Pro
    370                 375                 380

Arg Gly Thr Met Leu Ile Val Asn Gln Trp Ala Ile His His Asp Pro
385                 390                 395                 400

Lys Val Trp Asp Asp Pro Glu Thr Phe Lys Pro Glu Arg Phe Gln Gly
                405                 410                 415

Leu Glu Gly Thr Arg Asp Gly Phe Lys Leu Met Pro Phe Gly Ser Gly
            420                 425                 430

Arg Arg Gly Cys Pro Gly Glu Gly Leu Ala Ile Arg Leu Leu Gly Met
        435                 440                 445

Thr Leu Gly Ser Val Ile Gln Cys Phe Asp Trp Glu Arg Val Gly Asp
    450                 455                 460

Glu Met Val Asp Met Thr Glu Gly Leu Gly Val Thr Leu Pro Lys Ala
465                 470                 475                 480

Val Pro Leu Val Ala Lys Cys Lys Pro Arg Ser Glu Met Thr Asn Leu
                485                 490                 495

Leu Ser Glu Leu
            500

<210> SEQ ID NO 16
<211> LENGTH: 2124
<212> TYPE: DNA
<213> ORGANISM: Stevia rebaudiana

<400> SEQUENCE: 16
atgcaatcta actccgtgaa gatttcgccg cttgatctgg taactgcgct gtttagcggc      60
aaggttttgg acacatcgaa cgcatcggaa tcgggagaat ctgctatgct gccgactata     120
gcgatgatta tggagaatcg tgagctgttg atgatactca caacgtcggt tgctgtattg     180
```

```
atcggatgcg ttgtcgtttt ggtgtggcgg agatcgtcta cgaagaagtc ggcgttggag      240
ccaccggtga ttgtggttcc gaagagagtg caagaggagg aagttgatga tggtaagaag      300
aaagttacgg ttttcttcgg cacccaaact ggaacagctg aaggcttcgc taaggcactt      360
gttgaggaag ctaaagctcg atatgaaaag gctgtcttta agtaattgat tttggatgat      420
tatgctgctg atgacgatga gtatgaggag aaactaaaga agaatctttt ggcctttttc      480
tttttggcta cgtatggaga tggtgagcca acagataatg ctgccagatt ttataaatgg      540
tttactgagg gagatgcgaa aggagaatgg cttaataagc ttcaatatgg agtatttggt      600
ttgggtaaca gacaatatga acattttaac aagatcgcaa aagtggttga tgatggtctt      660
gtagaacagg gtgcaaagcg tcttgttcct gttggacttg agatgatga tcaatgtatt       720 gaagatgact tcaccgcatg gaaagagtta gtatggccgg agttggatca attacttcgt      780
gatgaggatg acacaactgt tgctactcca tacacagctg ctgttgcaga atatcgcgtt      840 gttttttcatg aaaaaccaga cgcgctttct gaagattata gttatacaaa tggccatgct      900
gttcatgatg ctcaacatcc atgcagatcc aacgtggctg tcaaaaagga acttcatagt      960
cctgaatctg accggtcttg cactcatctt gaatttgaca tctcgaacac cggactatca     1020
tatgaaactg gggaccatgt tggagtttac tgtgaaaact tgagtgaagt tgtgaatgat     1080
gctgaaagat tagtaggatt accaccagac acttactcct ccatccacac tgatagtgaa     1140
gacgggtcgc cacttggcgg agcctcattg ccgcctcctt tcccgccatg cactttaagg     1200
aaagcattga cgtgttatgc tgatgttttg agttctccca gaagtcggc tttgcttgca      1260 ctagctgctg atgccaccga tcccagtgaa gctgatagat tgaaatttct tgcatccccc     1320
gccggaaagg atgaatattc tcaatggata gttgcaagcc aaagaagtct ccttgaagtc     1380
atggaagcat tcccgtcagc taagccttca cttggtgttt tctttgcatc tgttgccccg     1440
cgcttacaac caagatacta ctctatttct tcctcaccca agatggcacc ggataggatt     1500
catgttacat gtgcattagt ctatgagaaa acacctgcag gccgcatcca caaggagtt      1560 tgttcaactt ggatgaagaa cgcagtgcct atgaccgaga gtcaagattg cagttgggcc     1620
ccaatatacg tccgaacatc caatttcaga ctaccatctg accctaaggt cccggttatc     1680
atgattggac ctggcactgg tttggctcct tttagaggtt ccttcaaga gcggttagct      1740 ttaaaggaag ccgaactgaa cctcggttta tccattttat tcttcggatg taggaatcgc     1800
aaagtggatt tcatatatga aaacgagctt aacaactttg tggagactgg tgctctttct     1860
gagcttattg ttgctttctc ccgtgaaggc ccgactaagg aatatgtgca acacaagatg     1920
agtgagaagg cttcggatat ctggaacttg ctttctgaag gagcatattt atacgtatgt     1980
ggtgatgcca aaggcatggc caaagatgta catcgaaccc tccacacaat tgtgcaagaa     2040
cagggatctc ttgactcgtc aaaggcagaa ctctacgtga agaatctaca aatgtcagga     2100
agatacctcc gtgacgtttg gtaa                                             2124
```

<210> SEQ ID NO 17
<211> LENGTH: 707
<212> TYPE: PRT
<213> ORGANISM: Stevia rebaudiana

<400> SEQUENCE: 17

```
Met Gln Ser Asn Ser Val Lys Ile Ser Pro Leu Asp Leu Val Thr Ala
1               5                   10                  15

Leu Phe Ser Gly Lys Val Leu Asp Thr Ser Asn Ala Ser Glu Ser Gly
            20                  25                  30
```

```
Glu Ser Ala Met Leu Pro Thr Ile Ala Met Ile Met Glu Asn Arg Glu
            35                  40                  45

Leu Leu Met Ile Leu Thr Thr Ser Val Ala Val Leu Ile Gly Cys Val
    50                  55                  60

Val Val Leu Val Trp Arg Arg Ser Ser Thr Lys Lys Ser Ala Leu Glu
65                  70                  75                  80

Pro Pro Val Ile Val Pro Lys Arg Val Gln Glu Glu Val Asp
                85                  90                  95

Asp Gly Lys Lys Lys Val Thr Val Phe Phe Gly Thr Gln Thr Gly Thr
                100                 105                 110

Ala Glu Gly Phe Ala Lys Ala Leu Val Glu Glu Ala Lys Ala Arg Tyr
                115                 120                 125

Glu Lys Ala Val Phe Lys Val Ile Asp Leu Asp Asp Tyr Ala Ala Asp
        130                 135                 140

Asp Asp Glu Tyr Glu Glu Lys Leu Lys Lys Glu Ser Leu Ala Phe Phe
145                 150                 155                 160

Phe Leu Ala Thr Tyr Gly Asp Gly Glu Pro Thr Asp Asn Ala Ala Arg
                165                 170                 175

Phe Tyr Lys Trp Phe Thr Glu Gly Asp Ala Lys Gly Glu Trp Leu Asn
            180                 185                 190

Lys Leu Gln Tyr Gly Val Phe Gly Leu Gly Asn Arg Gln Tyr Glu His
        195                 200                 205

Phe Asn Lys Ile Ala Lys Val Val Asp Asp Gly Leu Val Glu Gln Gly
        210                 215                 220

Ala Lys Arg Leu Val Pro Val Gly Leu Gly Asp Asp Gln Cys Ile
225                 230                 235                 240

Glu Asp Asp Phe Thr Ala Trp Lys Glu Leu Val Trp Pro Glu Leu Asp
                245                 250                 255

Gln Leu Leu Arg Asp Glu Asp Thr Thr Val Ala Thr Pro Tyr Thr
                260                 265                 270

Ala Ala Val Ala Glu Tyr Arg Val Val Phe His Glu Lys Pro Asp Ala
        275                 280                 285

Leu Ser Glu Asp Tyr Ser Tyr Thr Asn Gly His Ala Val His Asp Ala
        290                 295                 300

Gln His Pro Cys Arg Ser Asn Val Ala Val Lys Lys Glu Leu His Ser
305                 310                 315                 320

Pro Glu Ser Asp Arg Ser Cys Thr His Leu Glu Phe Asp Ile Ser Asn
                325                 330                 335

Thr Gly Leu Ser Tyr Glu Thr Gly Asp His Val Gly Val Tyr Cys Glu
            340                 345                 350

Asn Leu Ser Glu Val Val Asn Asp Ala Glu Arg Leu Val Gly Leu Pro
        355                 360                 365

Pro Asp Thr Tyr Ser Ser Ile His Thr Asp Ser Glu Asp Gly Ser Pro
    370                 375                 380

Leu Gly Gly Ala Ser Leu Pro Pro Phe Pro Cys Thr Leu Arg
385                 390                 395                 400

Lys Ala Leu Thr Cys Tyr Ala Asp Val Leu Ser Ser Pro Lys Lys Ser
                405                 410                 415

Ala Leu Leu Ala Leu Ala Ala His Ala Thr Asp Pro Ser Glu Ala Asp
            420                 425                 430

Arg Leu Lys Phe Leu Ala Ser Pro Ala Gly Lys Asp Glu Tyr Ser Gln
            435                 440                 445
```

Trp Ile Val Ala Ser Gln Arg Ser Leu Leu Glu Val Met Glu Ala Phe
    450                 455                 460

Pro Ser Ala Lys Pro Ser Leu Gly Val Phe Phe Ala Ser Val Ala Pro
465                 470                 475                 480

Arg Leu Gln Pro Arg Tyr Tyr Ser Ile Ser Ser Pro Lys Met Ala
                485                 490                 495

Pro Asp Arg Ile His Val Thr Cys Ala Leu Val Tyr Glu Lys Thr Pro
                500                 505                 510

Ala Gly Arg Ile His Lys Gly Val Cys Ser Thr Trp Met Lys Asn Ala
                515                 520                 525

Val Pro Met Thr Glu Ser Gln Asp Cys Ser Trp Ala Pro Ile Tyr Val
530                 535                 540

Arg Thr Ser Asn Phe Arg Leu Pro Ser Asp Pro Lys Val Pro Val Ile
545                 550                 555                 560

Met Ile Gly Pro Gly Thr Gly Leu Ala Pro Phe Arg Gly Phe Leu Gln
                565                 570                 575

Glu Arg Leu Ala Leu Lys Glu Ala Gly Thr Asp Leu Gly Leu Ser Ile
                580                 585                 590

Leu Phe Phe Gly Cys Arg Asn Arg Lys Val Asp Phe Ile Tyr Glu Asn
                595                 600                 605

Glu Leu Asn Asn Phe Val Glu Thr Gly Ala Leu Ser Glu Leu Ile Val
        610                 615                 620

Ala Phe Ser Arg Glu Gly Pro Thr Lys Glu Tyr Val Gln His Lys Met
625                 630                 635                 640

Ser Glu Lys Ala Ser Asp Ile Trp Asn Leu Leu Ser Glu Gly Ala Tyr
                645                 650                 655

Leu Tyr Val Cys Gly Asp Ala Lys Gly Met Ala Lys Asp Val His Arg
                660                 665                 670

Thr Leu His Thr Ile Val Gln Glu Gln Gly Ser Leu Asp Ser Ser Lys
        675                 680                 685

Ala Glu Leu Tyr Val Lys Asn Leu Gln Met Ser Gly Arg Tyr Leu Arg
        690                 695                 700

Asp Val Trp
705

<210> SEQ ID NO 18
<211> LENGTH: 2133
<212> TYPE: DNA
<213> ORGANISM: Artificial Sequence
<220> FEATURE:
<223> OTHER INFORMATION: Codon optimized

<400> SEQUENCE: 18
atgcaatcag attcagtcaa agtctctcca tttgatttgg tttccgctgc tatgaatggc      60
aaggcaatgg aaaagttgaa cgctagtgaa tctgaagatc aacaacatt gcctgcacta     120 aagatgctag ttgaaaatag agaattgttg acactgttca aacttccttc gcagttctt     180 attgggtgtc ttgtatttct aatgtggaga cgttcatcct ctaaaaagct ggtacaagat     240
ccagttccac aagttatcgt tgtaaagaag aaagagaagg agtcagaggt tgatgacggg     300
aaaaagaaag tttctatttt ctacggcaca caaacaggac tgccgaaggt ttttgctaaa     360
gcattagtcg aggaagcaaa agtgagatat gaaaagacct ctttcaaggt tatcgatcta     420
gatgactacg ctgcagatga tgatgaatat gaggaaaaac tgaaaaagga atccttagcc     480
ttcttcttct tggccacata cggtgatggt gaacctactg ataatgctgc taacttctac     540

|  |  |
|---|---|
| aagtggttca cagaaggcga cgataaaggt gaatggctga aaaagttaca atacggagta | 600 |
| tttggtttag gtaacagaca atatgaacat ttcaacaaga tcgctattgt agttgatgat | 660 |
| aaacttactg aaatgggagc caaaagatta gtaccagtag gattagggga tgatgatcag | 720 |
| tgtatagaag atgacttcac cgcctggaag gaattggtat ggccagaatt ggatcaactt | 780 |
| ttaagggacg aagatgatac ttctgtgact accccataca ctgcagccgt attggagtac | 840 |
| agagtggttt accatgataa accagcagac tcatatgctg aagatcaaac ccatacaaac | 900 |
| ggtcatgttg ttcatgatgc acagcatcct tcaagatcta atgtggcttt caaaaaggaa | 960 |
| ctacacacct ctcaatcaga taggtcttgt actcacttag aattcgatat ttctcacaca | 1020 |
| ggactgtctt acgaaactgg cgatcacgtt ggcgtttatt ccgagaactt gtccgaagtt | 1080 |
| gtcgatgaag cactaaaact gttagggtta tcaccagaca catacttctc agtccatgct | 1140 |
| gataaggagg atgggacacc tatcggtggt gcttcactac caccaccttt tcctccttgc | 1200 |
| acattgagag acgctctaac cagatacgca gatgtcttat cctcacctaa aaaggtagct | 1260 |
| ttgctggcat tggctgctca tgctagtgat cctagtgaag ccgataggtt aaagttcctg | 1320 |
| gcttcaccag ccggaaaaga tgaatatgca caatggatcg tcgccaacca acgttctttg | 1380 |
| ctagaagtga tgcaaagttt tccatctgcc aagcctccat taggtgtgtt cttcgcagca | 1440 |
| gtagctccac gtttacaacc aagatactac tctatcagtt catctcctaa gatgtctcct | 1500 |
| aacagaaatac atgttacatg tgctttggtg tacgagacta ctccagcagg cagaattcac | 1560 |
| agaggattgt gttcaacctg gatgaaaaat gctgtccctt aacagagtc acctgattgc | 1620 |
| tctcaagcat ccatttttcgt tagaacatca aatttcagac ttccagtgga tccaaaagtt | 1680 |
| ccagtcatta tgataggacc aggcactggt cttgccccat tcaggggctt tcttcaagag | 1740 |
| agattggcct tgaaggaatc tggtacagaa ttgggttctt ctatcttttt ctttggttgc | 1800 |
| cgtaatagaa aagttgactt tatctacgag gacgagctta caattttgt tgagacagga | 1860 |
| gcattgtcag aattgatcgt cgcatttca agagaaggga ctgccaaaga gtacgttcag | 1920 |
| cacaagatga gtcaaaaagc ctccgatata tggaaacttc taagtgaagg tgcctatctt | 1980 |
| tatgtctgtg gcgatgcaaa gggcatggcc aaggatgtcc atagaactct gcatacaatt | 2040 |
| gttcaggaac aagggagtct ggattcttcc aaggctgaat tgtacgtcaa aaacttacag | 2100 |
| atgtctggaa gatacttaag agatgtttgg taa | 2133 |

<210> SEQ ID NO 19
<211> LENGTH: 710
<212> TYPE: PRT
<213> ORGANISM: Stevia rebaudiana

<400> SEQUENCE: 19

```
Met Gln Ser Asp Ser Val Lys Val Ser Pro Phe Asp Leu Val Ser Ala
1               5                   10                  15

Ala Met Asn Gly Lys Ala Met Glu Lys Leu Asn Ala Ser Glu Ser Glu
            20                  25                  30

Asp Pro Thr Thr Leu Pro Ala Leu Lys Met Leu Val Glu Asn Arg Glu
        35                  40                  45

Leu Leu Thr Leu Phe Thr Thr Ser Phe Ala Val Leu Ile Gly Cys Leu
    50                  55                  60

Val Phe Leu Met Trp Arg Arg Ser Ser Lys Lys Leu Val Gln Asp
65                  70                  75                  80

Pro Val Pro Gln Val Ile Val Val Lys Lys Glu Lys Glu Ser Glu
                85                  90                  95
```

```
Val Asp Asp Gly Lys Lys Val Ser Ile Phe Tyr Gly Thr Gln Thr
            100                 105                 110

Gly Thr Ala Glu Gly Phe Ala Lys Ala Leu Val Glu Ala Lys Val
            115                 120                 125

Arg Tyr Glu Lys Thr Ser Phe Lys Val Ile Asp Leu Asp Asp Tyr Ala
            130                 135                 140

Ala Asp Asp Asp Glu Tyr Glu Glu Lys Leu Lys Lys Glu Ser Leu Ala
145                 150                 155                 160

Phe Phe Phe Leu Ala Thr Tyr Gly Asp Gly Glu Pro Thr Asp Asn Ala
                165                 170                 175

Ala Asn Phe Tyr Lys Trp Phe Thr Glu Gly Asp Lys Gly Glu Trp
            180                 185                 190

Leu Lys Lys Leu Gln Tyr Gly Val Phe Gly Leu Gly Asn Arg Gln Tyr
            195                 200                 205

Glu His Phe Asn Lys Ile Ala Ile Val Val Asp Asp Lys Leu Thr Glu
    210                 215                 220

Met Gly Ala Lys Arg Leu Val Pro Val Gly Leu Gly Asp Asp Asp Gln
225                 230                 235                 240

Cys Ile Glu Asp Asp Phe Thr Ala Trp Lys Glu Leu Val Trp Pro Glu
                245                 250                 255

Leu Asp Gln Leu Leu Arg Asp Glu Asp Thr Ser Val Thr Thr Pro
            260                 265                 270

Tyr Thr Ala Ala Val Leu Glu Tyr Arg Val Val Tyr His Asp Lys Pro
            275                 280                 285

Ala Asp Ser Tyr Ala Glu Asp Gln Thr His Thr Asn Gly His Val Val
            290                 295                 300

His Asp Ala Gln His Pro Ser Arg Ser Asn Val Ala Phe Lys Lys Glu
305                 310                 315                 320

Leu His Thr Ser Gln Ser Asp Arg Ser Cys Thr His Leu Glu Phe Asp
                325                 330                 335

Ile Ser His Thr Gly Leu Ser Tyr Glu Thr Gly Asp His Val Gly Val
            340                 345                 350

Tyr Ser Glu Asn Leu Ser Glu Val Val Asp Glu Ala Leu Lys Leu Leu
            355                 360                 365

Gly Leu Ser Pro Asp Thr Tyr Phe Ser Val His Ala Asp Lys Glu Asp
370                 375                 380

Gly Thr Pro Ile Gly Gly Ala Ser Leu Pro Pro Phe Pro Pro Cys
385                 390                 395                 400

Thr Leu Arg Asp Ala Leu Thr Arg Tyr Ala Asp Val Leu Ser Ser Pro
                405                 410                 415

Lys Lys Val Ala Leu Leu Ala Leu Ala Ala His Ala Ser Asp Pro Ser
            420                 425                 430

Glu Ala Asp Arg Leu Lys Phe Leu Ala Ser Pro Ala Gly Lys Asp Glu
            435                 440                 445

Tyr Ala Gln Trp Ile Val Ala Asn Gln Arg Ser Leu Leu Glu Val Met
            450                 455                 460

Gln Ser Phe Pro Ser Ala Lys Pro Pro Leu Gly Val Phe Phe Ala Ala
465                 470                 475                 480

Val Ala Pro Arg Leu Gln Pro Arg Tyr Tyr Ser Ile Ser Ser Ser Pro
                485                 490                 495

Lys Met Ser Pro Asn Arg Ile His Val Thr Cys Ala Leu Val Tyr Glu
            500                 505                 510
```

```
Thr Thr Pro Ala Gly Arg Ile His Arg Gly Leu Cys Ser Thr Trp Met
            515                 520                 525

Lys Asn Ala Val Pro Leu Thr Glu Ser Pro Asp Cys Ser Gln Ala Ser
530                 535                 540

Ile Phe Val Arg Thr Ser Asn Phe Arg Leu Pro Val Asp Pro Lys Val
545                 550                 555                 560

Pro Val Ile Met Ile Gly Pro Gly Thr Gly Leu Ala Pro Phe Arg Gly
                565                 570                 575

Phe Leu Gln Glu Arg Leu Ala Leu Lys Glu Ser Gly Thr Glu Leu Gly
                580                 585                 590

Ser Ser Ile Phe Phe Gly Cys Arg Asn Arg Lys Val Asp Phe Ile
                595                 600                 605

Tyr Glu Asp Glu Leu Asn Asn Phe Val Glu Thr Gly Ala Leu Ser Glu
            610                 615                 620

Leu Ile Val Ala Phe Ser Arg Glu Gly Thr Ala Lys Glu Tyr Val Gln
625                 630                 635                 640

His Lys Met Ser Gln Lys Ala Ser Asp Ile Trp Lys Leu Leu Ser Glu
                645                 650                 655

Gly Ala Tyr Leu Tyr Val Cys Gly Asp Ala Lys Gly Met Ala Lys Asp
                660                 665                 670

Val His Arg Thr Leu His Thr Ile Val Gln Glu Gln Gly Ser Leu Asp
                675                 680                 685

Ser Ser Lys Ala Glu Leu Tyr Val Lys Asn Leu Gln Met Ser Gly Arg
                690                 695                 700

Tyr Leu Arg Asp Val Trp
705                 710

<210> SEQ ID NO 20
<211> LENGTH: 511
<212> TYPE: PRT
<213> ORGANISM: Rubus suavissimus

<400> SEQUENCE: 20

Met Ala Thr Leu Leu Glu His Phe Gln Ala Met Pro Phe Ala Ile Pro
1               5                   10                  15

Ile Ala Leu Ala Ala Leu Ser Trp Leu Phe Leu Phe Tyr Ile Lys Val
                20                  25                  30

Ser Phe Phe Ser Asn Lys Ser Ala Gln Ala Lys Leu Pro Pro Val Pro
            35                  40                  45

Val Val Pro Gly Leu Pro Val Ile Gly Asn Leu Leu Gln Leu Lys Glu
50                  55                  60

Lys Lys Pro Tyr Gln Thr Phe Thr Arg Trp Ala Glu Glu Tyr Gly Pro
65                  70                  75                  80

Ile Tyr Ser Ile Arg Thr Gly Ala Ser Thr Met Val Val Leu Asn Thr
                85                  90                  95

Thr Gln Val Ala Lys Glu Ala Met Val Thr Arg Tyr Leu Ser Ile Ser
            100                 105                 110

Thr Arg Lys Leu Ser Asn Ala Leu Lys Ile Leu Thr Ala Asp Lys Cys
        115                 120                 125

Met Val Ala Ile Ser Asp Tyr Asn Asp Phe His Lys Met Ile Lys Arg
    130                 135                 140

Tyr Ile Leu Ser Asn Val Leu Gly Pro Ser Ala Gln Lys Arg His Arg
145                 150                 155                 160

Ser Asn Arg Asp Thr Leu Arg Ala Asn Val Cys Ser Arg Leu His Ser
                165                 170                 175
```

```
Gln Val Lys Asn Ser Pro Arg Glu Ala Val Asn Phe Arg Arg Val Phe
            180                 185                 190

Glu Trp Glu Leu Phe Gly Ile Ala Leu Lys Gln Ala Phe Gly Lys Asp
        195                 200                 205

Ile Glu Lys Pro Ile Tyr Val Glu Leu Gly Thr Thr Leu Ser Arg
    210                 215                 220

Asp Glu Ile Phe Lys Val Leu Val Leu Asp Ile Met Glu Gly Ala Ile
225                 230                 235                 240

Glu Val Asp Trp Arg Asp Phe Phe Pro Tyr Leu Arg Trp Ile Pro Asn
                245                 250                 255

Thr Arg Met Glu Thr Lys Ile Gln Arg Leu Tyr Phe Arg Arg Lys Ala
            260                 265                 270

Val Met Thr Ala Leu Ile Asn Glu Gln Lys Lys Arg Ile Ala Ser Gly
        275                 280                 285

Glu Glu Ile Asn Cys Tyr Ile Asp Phe Leu Leu Lys Glu Gly Lys Thr
    290                 295                 300

Leu Thr Met Asp Gln Ile Ser Met Leu Leu Trp Glu Thr Val Ile Glu
305                 310                 315                 320

Thr Ala Asp Thr Thr Met Val Thr Thr Glu Trp Ala Met Tyr Glu Val
                325                 330                 335

Ala Lys Asp Ser Lys Arg Gln Asp Arg Leu Tyr Gln Glu Ile Gln Lys
            340                 345                 350

Val Cys Gly Ser Glu Met Val Thr Glu Glu Tyr Leu Ser Gln Leu Pro
        355                 360                 365

Tyr Leu Asn Ala Val Phe His Glu Thr Leu Arg Lys His Ser Pro Ala
    370                 375                 380

Ala Leu Val Pro Leu Arg Tyr Ala His Glu Asp Thr Gln Leu Gly Gly
385                 390                 395                 400

Tyr Tyr Ile Pro Ala Gly Thr Glu Ile Ala Ile Asn Ile Tyr Gly Cys
                405                 410                 415

Asn Met Asp Lys His Gln Trp Glu Ser Pro Glu Glu Trp Lys Pro Glu
            420                 425                 430

Arg Phe Leu Asp Pro Lys Phe Asp Pro Met Asp Leu Tyr Lys Thr Met
        435                 440                 445

Ala Phe Gly Ala Gly Lys Arg Val Cys Ala Gly Ser Leu Gln Ala Met
    450                 455                 460

Leu Ile Ala Cys Pro Thr Ile Gly Arg Leu Val Gln Glu Phe Glu Trp
465                 470                 475                 480

Lys Leu Arg Asp Gly Glu Glu Asn Val Asp Thr Val Gly Leu Thr
                485                 490                 495

Thr His Lys Arg Tyr Pro Met His Ala Ile Leu Lys Pro Arg Ser
            500                 505                 510

<210> SEQ ID NO 21
<211> LENGTH: 523
<212> TYPE: PRT
<213> ORGANISM: Rubus suavissimus

<400> SEQUENCE: 21

Met Glu Val Thr Val Ala Ser Ser Val Ala Leu Ser Leu Val Phe Ile
1               5                   10                  15

Ser Ile Val Val Arg Trp Ala Trp Ser Val Val Asn Trp Val Trp Phe
            20                  25                  30

Lys Pro Lys Lys Leu Glu Arg Phe Leu Arg Glu Gln Gly Leu Lys Gly
```

```
            35                  40                  45
Asn Ser Tyr Arg Phe Leu Tyr Gly Asp Met Lys Glu Asn Ser Ile Leu
 50                  55                  60

Leu Lys Gln Ala Arg Ser Lys Pro Met Asn Leu Ser Thr Ser His Asp
 65                  70                  75                  80

Ile Ala Pro Gln Val Thr Pro Phe Val Asp Gln Thr Val Lys Ala Tyr
                     85                  90                  95

Gly Lys Asn Ser Phe Asn Trp Val Gly Pro Ile Pro Arg Val Asn Ile
                100                 105                 110

Met Asn Pro Glu Asp Leu Lys Asp Val Leu Thr Lys Asn Val Asp Phe
            115                 120                 125

Val Lys Pro Ile Ser Asn Pro Leu Ile Lys Leu Leu Ala Thr Gly Ile
        130                 135                 140

Ala Ile Tyr Glu Gly Glu Lys Trp Thr Lys His Arg Arg Ile Ile Asn
145                 150                 155                 160

Pro Thr Phe His Ser Glu Arg Leu Lys Arg Met Leu Pro Ser Phe His
                165                 170                 175

Gln Ser Cys Asn Glu Met Val Lys Glu Trp Glu Ser Leu Val Ser Lys
                180                 185                 190

Glu Gly Ser Ser Cys Glu Leu Asp Val Trp Pro Phe Leu Glu Asn Met
            195                 200                 205

Ser Ala Asp Val Ile Ser Arg Thr Ala Phe Gly Thr Ser Tyr Lys Lys
210                 215                 220

Gly Gln Lys Ile Phe Glu Leu Leu Arg Glu Gln Val Ile Tyr Val Thr
225                 230                 235                 240

Lys Gly Phe Gln Ser Phe Tyr Ile Pro Gly Trp Arg Phe Leu Pro Thr
                245                 250                 255

Lys Met Asn Lys Arg Met Asn Glu Ile Asn Glu Ile Lys Gly Leu
                260                 265                 270

Ile Arg Gly Ile Ile Ile Asp Arg Glu Gln Ile Ile Lys Ala Gly Glu
            275                 280                 285

Glu Thr Asn Asp Asp Leu Leu Gly Ala Leu Met Glu Ser Asn Leu Lys
        290                 295                 300

Asp Ile Arg Glu His Gly Lys Asn Asn Lys Asn Val Gly Met Ser Ile
305                 310                 315                 320

Glu Asp Val Ile Gln Glu Cys Lys Leu Phe Tyr Phe Ala Gly Gln Glu
                325                 330                 335

Thr Thr Ser Val Leu Leu Ala Trp Thr Met Val Leu Leu Gly Gln Asn
            340                 345                 350

Gln Asn Trp Gln Asp Arg Ala Arg Gln Glu Val Leu Gln Val Phe Gly
        355                 360                 365

Ser Ser Lys Pro Asp Phe Asp Gly Leu Ala His Leu Lys Val Val Thr
        370                 375                 380

Met Ile Leu Leu Glu Val Leu Arg Leu Tyr Pro Pro Val Ile Glu Leu
385                 390                 395                 400

Ile Arg Thr Ile His Lys Lys Thr Gln Leu Gly Lys Leu Ser Leu Pro
                405                 410                 415

Glu Gly Val Glu Val Arg Leu Pro Thr Leu Leu Ile His His Asp Lys
            420                 425                 430

Glu Leu Trp Gly Asp Asp Ala Asn Gln Phe Asn Pro Glu Arg Phe Ser
        435                 440                 445

Glu Gly Val Ser Lys Ala Thr Lys Asn Arg Leu Ser Phe Phe Pro Phe
450                 455                 460
```

```
Gly Ala Gly Pro Arg Ile Cys Ile Gly Gln Asn Phe Ser Met Met Glu
465                 470                 475                 480

Ala Lys Leu Ala Leu Ala Leu Ile Leu Gln His Phe Thr Phe Glu Leu
            485                 490                 495

Ser Pro Ser His Ala His Ala Pro Ser His Arg Ile Thr Leu Gln Pro
        500                 505                 510

Gln Tyr Gly Val Arg Ile Ile Leu His Arg Arg
    515                 520

<210> SEQ ID NO 22
<211> LENGTH: 701
<212> TYPE: PRT
<213> ORGANISM: Siraitia grosvenorii

<400> SEQUENCE: 22

Met Lys Val Ser Pro Phe Glu Phe Met Ser Ala Ile Ile Lys Gly Arg
1               5                   10                  15

Met Asp Pro Ser Asn Ser Ser Phe Glu Ser Thr Gly Glu Val Ala Ser
            20                  25                  30

Val Ile Phe Glu Asn Arg Glu Leu Val Ala Ile Leu Thr Thr Ser Ile
        35                  40                  45

Ala Val Met Ile Gly Cys Phe Val Val Leu Met Trp Arg Arg Ala Gly
    50                  55                  60

Ser Arg Lys Val Lys Asn Val Glu Leu Pro Lys Pro Leu Ile Val His
65                  70                  75                  80

Glu Pro Glu Pro Glu Val Glu Asp Gly Lys Lys Val Ser Ile Phe
                85                  90                  95

Phe Gly Thr Gln Thr Gly Thr Ala Glu Gly Phe Ala Lys Ala Leu Ala
            100                 105                 110

Asp Glu Ala Lys Ala Arg Tyr Glu Lys Ala Thr Phe Arg Val Val Asp
        115                 120                 125

Leu Asp Asp Tyr Ala Ala Asp Asp Gln Tyr Glu Glu Lys Leu Lys
    130                 135                 140

Asn Glu Ser Phe Ala Val Phe Leu Leu Ala Thr Tyr Gly Asp Gly Glu
145                 150                 155                 160

Pro Thr Asp Asn Ala Ala Arg Phe Tyr Lys Trp Phe Ala Glu Gly Lys
                165                 170                 175

Glu Arg Gly Glu Trp Leu Gln Asn Leu His Tyr Ala Val Phe Gly Leu
            180                 185                 190

Gly Asn Arg Gln Tyr Glu His Phe Asn Lys Ile Ala Lys Val Ala Asp
        195                 200                 205

Glu Leu Leu Glu Ala Gln Gly Gly Asn Arg Leu Val Lys Val Gly Leu
    210                 215                 220

Gly Asp Asp Asp Gln Cys Ile Glu Asp Asp Phe Ser Ala Trp Arg Glu
225                 230                 235                 240

Ser Leu Trp Pro Glu Leu Asp Met Leu Leu Arg Asp Glu Asp Asp Ala
                245                 250                 255

Thr Thr Val Thr Thr Pro Tyr Thr Ala Ala Val Leu Glu Tyr Arg Val
            260                 265                 270

Val Phe His Asp Ser Ala Asp Val Ala Ala Glu Asp Lys Ser Trp Ile
        275                 280                 285

Asn Ala Asn Gly His Ala Val His Asp Ala Gln His Pro Phe Arg Ser
    290                 295                 300

Asn Val Val Val Arg Lys Glu Leu His Thr Ser Ala Ser Asp Arg Ser
```

-continued

```
            305                 310                 315                 320
        Cys Ser His Leu Glu Phe Asn Ile Ser Gly Ser Ala Leu Asn Tyr Glu
                        325                 330                 335

Thr Gly Asp His Val Gly Val Tyr Cys Glu Asn Leu Thr Glu Thr Val
                        340                 345                 350

Asp Glu Ala Leu Asn Leu Leu Gly Leu Ser Pro Glu Thr Tyr Phe Ser
                        355                 360                 365

Ile Tyr Thr Asp Asn Glu Asp Gly Thr Pro Leu Gly Gly Ser Ser Leu
                370                 375                 380

Pro Pro Pro Phe Pro Ser Cys Thr Leu Arg Thr Ala Leu Thr Arg Tyr
        385                 390                 395                 400

Ala Asp Leu Leu Asn Ser Pro Lys Lys Ser Ala Leu Leu Ala Leu Ala
                        405                 410                 415

Ala His Ala Ser Asn Pro Val Glu Ala Asp Arg Leu Arg Tyr Leu Ala
                        420                 425                 430

Ser Pro Ala Gly Lys Asp Glu Tyr Ala Gln Ser Val Ile Gly Ser Gln
                        435                 440                 445

Lys Ser Leu Leu Glu Val Met Ala Glu Phe Pro Ser Ala Lys Pro Pro
                450                 455                 460

Leu Gly Val Phe Phe Ala Val Ala Pro Arg Leu Gln Pro Arg Phe
        465                 470                 475                 480

Tyr Ser Ile Ser Ser Ser Pro Arg Met Ala Pro Ser Arg Ile His Val
                        485                 490                 495

Thr Cys Ala Leu Val Tyr Asp Lys Met Pro Thr Gly Arg Ile His Lys
                        500                 505                 510

Gly Val Cys Ser Thr Trp Met Lys Asn Ser Val Pro Met Glu Lys Ser
                        515                 520                 525

His Glu Cys Ser Trp Ala Pro Ile Phe Val Arg Gln Ser Asn Phe Lys
                        530                 535                 540

Leu Pro Ala Glu Ser Lys Val Pro Ile Ile Met Val Gly Pro Gly Thr
        545                 550                 555                 560

Gly Leu Ala Pro Phe Arg Gly Phe Leu Gln Glu Arg Leu Ala Leu Lys
                        565                 570                 575

Glu Ser Gly Val Glu Leu Gly Pro Ser Ile Leu Phe Phe Gly Cys Arg
                        580                 585                 590

Asn Arg Arg Met Asp Tyr Ile Tyr Glu Asp Glu Leu Asn Asn Phe Val
                        595                 600                 605

Glu Thr Gly Ala Leu Ser Glu Leu Val Ile Ala Phe Ser Arg Glu Gly
                610                 615                 620

Pro Thr Lys Glu Tyr Val Gln His Lys Met Ala Glu Lys Ala Ser Asp
        625                 630                 635                 640

Ile Trp Asn Leu Ile Ser Glu Gly Ala Tyr Leu Tyr Val Cys Gly Asp
                        645                 650                 655

Ala Lys Gly Met Ala Lys Asp Val His Arg Thr Leu His Thr Ile Met
                        660                 665                 670

Gln Glu Gln Gly Ser Leu Asp Ser Ser Lys Ala Glu Ser Met Val Lys
                        675                 680                 685

Asn Leu Gln Met Asn Gly Arg Tyr Leu Arg Asp Val Trp
                690                 695                 700
```

FERMENTATION METHODS FOR PRODUCING STEVIOL GLYCOSIDES WITH MULTI-PHASE FEEDING

CROSS-REFERENCE TO RELATED APPLICATIONS

This application claims priority to U.S. Provisional Application No. 62/168,372 filed May 29, 2015, herein incorporated by reference in its entirety.

REFERENCE TO SEQUENCE LISTING

This application is a national phase application of PCT/US2016/034826, filed May 27, 2016, and entitled FERMENTATION METHODS FOR PRODUCING STEVIOL GLYCOSIDES WITH MULTI-PHASE FEEDING, which claims the benefit of U.S. Provisional Patent Application Ser. No. 62/168,3722 filed May 29, 2015, and entitled FERMENTATION METHODS FOR PRODUCING STEVIOL GLYCOSIDES WITH MULTI-PHASE FEEDING, each of which is hereby incorporated by reference in its entirety.

FIELD

The present invention relates to fermentation methods for producing steviol glycosides, fermentation compositions, and steviol glycoside composition produced by fermentation.

BACKGROUND

Sugars, such as sucrose, fructose and glucose, are utilized to provide a pleasant taste to beverages, foods, pharmaceuticals, and oral hygienic/cosmetic products. Sucrose, in particular, imparts a taste preferred by consumers. Although sucrose provides superior sweetness characteristics, it is caloric. Non-caloric or lower caloric sweeteners have been introduced to satisfy consumer demand, and there is desire for these types of sweeteners that have favorable taste characteristics.

Stevia is a genus of about 240 species of herbs and shrubs in the sunflower family (Asteraceae), native to subtropical and tropical regions from western North America to South America. The species Stevia rebaudiana, commonly known as sweetleaf, sweet leaf, sugarleaf, or simply stevia, is widely grown for its sweet leaves. Stevia-based sweeteners may be obtained by extracting one or more sweet compounds from the leaves. Many of these compounds are steviol glycosides, which are glycosides of steviol, a diterpene compound. These diterpene glycosides are about 150 to 450 times sweeter than sugar. Steviol glycosides differ from each other by sweetness power as well as other sensory features contributing to taste quality such as bitterness, lingering aftertaste and the like. See Kinghorn, A. D., Stevia: The genus Stevia, Taylor & Francis, London (2002).

Examples of steviol glycosides are described in WO 2013/096420 (see, e.g., listing in FIG. 1); and in Ohta et. al., "Characterization of Novel Steviol Glycosides from Leaves of Stevia rebaudiana Morita," J. Appl. Glycosi., 57, 199-209 (2010) (See, e.g., Table 4 at p. 204). Structurally, the diterpene glycosides are characterized by a single core structure, steviol, and differ by the presence of carbohydrate residues at positions C13 and C19, as presented in FIGS. 2a-2k. See also PCT Patent Publication WO 20013/096420.

Typically, on a dry weight basis, the four major steviol glycosides found in the leaves of Stevia are dulcoside A (0.3%), rebaudioside C (0.6-1.0%), rebaudioside A (3.8%) and stevioside (9.1%). Other glycosides identified in Stevia extract include one or more of rebaudioside B, D, E, F, G, H, I, J, K, L, M, N, O, steviolbioside and rubusoside.

While the major steviol glycoside Reb A is commonly used as sweetener in beverage applications it has off-taste issues. More recently, there has been focus on certain minor steviol glycosides which have better taste properties. For example, rebaudioside M has higher sweetness intensity and is more potent than other steviol glycosides (e.g., see Prakash, I., et al. (2013) Nat. Prod. Commun., 8: 1523-1526, and WO 2013/096420). Rebaudioside D tastes about 200-220 times sweeter than sucrose and in a sensory evaluation it had a slow onset of sweetness and was very clean, namely sweeter overall than sucrose, less sweet lingering aftertaste compared to sucrose (e.g., see Prakash, I., et al. (2012) Int. J. Mol. Sci., 13:15126-15136).

Molecular techniques have been used to prepare recombinant organisms capable of synthesizing steviol glycosides via fermentation. For example, recombinant strains of Saccharomyces cerevisiae having multiple transgenes encoding enzymes involved in steviol glycoside synthesis have been used for the production of rebaudioside M and rebaudioside D (see, for example, WO2014/122227). However, current fermentation methods using recombinant organisms do not adequately provide desirable steviol glycoside production rates, and also are associated with generation of large amounts of biomass and longer fermentation times to achieve desired steviol glycoside titers.

SUMMARY

The present invention generally relates to methods for producing steviol glycosides using engineered yeast, as well as fermentation compositions, and fermentation products that include one or more steviol glycosides. Fermentation conditions of the disclosure can promote one or more of the following: increased steviol glycoside titers from the engineered yeast, increased cell activity including increased steviol glycoside production rates, increased yield, reduced fermentation times, and reduced biomass concentrations. In exemplary embodiments the methods can be used for the production of steviol glycosides such as rebaudioside M, rebaudioside D, rebaudioside A, rebaudioside B, and combinations thereof.

One embodiment of the invention provides a method for producing steviol glycoside(s), which includes:
 (a) growing engineered yeast capable of producing one or more steviol glycoside(s) in a medium, wherein the engineered yeast is grown at one or more growth rate(s) (dilution rate(s)) within a first range; and wherein a composition comprising glucose is added to the medium according to a first mode; and
 (b) fermenting the medium with the engineered yeast to produce the one or more steviol glycoside(s), wherein during fermenting, a composition comprising glucose is added to the medium according to a second mode that is different than the first mode, and during fermenting the yeast grow at one or more growth rate(s) (dilution rate(s)) within a second range, wherein the second range is less than the first range.

Another embodiment of the invention provides a method for producing steviol glycoside(s), which includes:
 at least steps (a) and (b) that involve the growth and fermentation of engineered yeast. In step (a) (i.e., a first phase) engineered yeast capable of producing one or more steviol glycoside(s) are grown in a medium at one or more growth rate(s) (dilution rate(s)) within a first range. Also in step (a) a composition comprising glucose is added to the medium according to a first mode that causes the yeast to grow within the first range. In step (b) (i.e., a second phase) the engineered yeast are fermented to produce the one or more steviol glycoside(s) where a composition comprising glucose is added to the medium according to a second mode that is different than the first mode. During step b), adding according to the second mode causes the yeast grow at one or more growth rate(s) (dilution rate(s)) within a second range which is less than the first range.

In an exemplary method, the yeast have a growth rate in step (a) in the range of about 0.06 $h^{-1}$ to about 0.15 $h^{-1}$, and a growth rate in step (b) in the range of about 0.015 $h^{-1}$ to about 0.09 $h^{-1}$. The change in growth rate from step (a) to step (b) can be caused by a change in "mode" of addition, such as by changing the rate of addition of a glucose-containing composition to the media, or changing how the glucose-containing composition is added to the media, such as providing a non-constant rate of feeding in step (a) and then a constant rate of feeding in step (b).

In another exemplary method, the engineered yeast are grown to a biomass amount in the range of 5 g dcw/L to 60 g dcw/L in step (a) and then to a biomass amount that does not exceed 150 g dcw/L in step (b).

In still other exemplary methods, the engineered yeast are grown by controlling the glucose feed rates based on a Respiratory Quotient (RQ), oxygen uptake rate (OUR), carbon dioxide evolution rate (CER) or combinations thereof. In some exemplary methods, the glucose is adjusted during the fermentation phase to an RQ that is within a range of from about 0.5 to about 2.0.

The invention also provides a fermentation medium comprising steviol glycoside(s) obtained according to the method of the disclosure, and also a steviol glycoside composition obtained from the fermentation medium.

DETAILED DESCRIPTION

Figure 1:
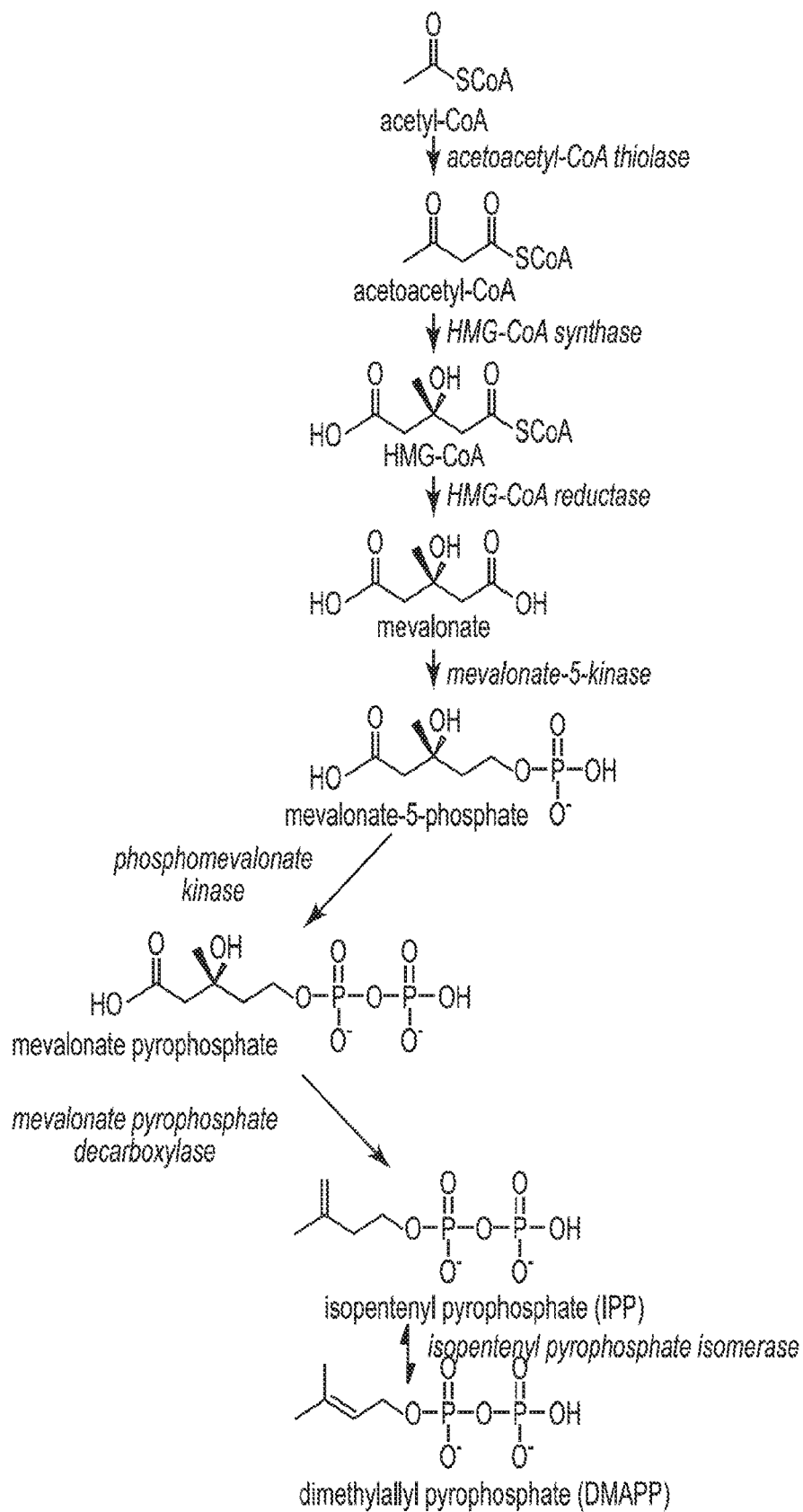
FIG. 1 shows a representative mevalonate pathway.

Embodiments of the disclosure described herein are not intended to be exhaustive or to limit the invention to the precise forms disclosed in the following detailed description. Rather a purpose of the embodiments chosen and described is so that the appreciation and understanding by others skilled in the art of the principles and practices of the present invention can be facilitated.

Fermentation methods of the disclosure use engineered yeast capable of producing steviol glycosides. An engineered yeast capable of producing steviol glycosides can include one or more exogenous nucleic acids that encode enzyme(s) that promote formation of one or more steviol glycosides in the cell.

As used herein, the term "steviol glycoside(s)" refers to glycosides of steviol. Exemplary steviol glycoside, include, but not are not limited to, rebaudioside A, rebaudioside B, rebaudioside C, rebaudioside D, rebaudioside E, rebaudioside F, rebaudioside G, rebaudioside H, rebaudioside I, rebaudioside J, rebaudioside K, rebaudioside L, rebaudioside M, rebaudioside N, rebaudioside O, stevioside, steviolbioside, dulcoside A, rubusoside. Engineered yeast can produce steviol glycosides that are the same as steviol glycosides found in nature ("naturally occurring") as well as steviol glycosides that are not found in nature. Steviol glycosides can be formed in an engineered yeast by enzymatic processes.

Structurally, steviol glycosides have a central molecular moiety, which is a single steviol base, and glucopyranosyl residues attached to the C13 and/or C19 atoms of the steviol base, according to the atom numbering on the base shown below. That is, glucopyranosyl residues represent groups $R_2$ and $R_1$ in the following formula:

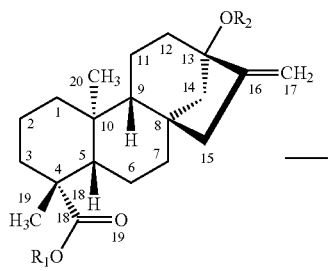

Table A below shows the various steviol glycosides and the corresponding $R_1$ and $R_2$ groups:

TABLE A

| Compound name | $R_1$ (C-19) | $R_2$ (C-13) |
|---|---|---|
| Steviol | H | H |
| Stevioside | β-Glu | β-Glu-β-Glu (2 -> 1) |
| Rebaudioside A | β-Glu | β-Glu-β-Glu (2 -> 1)<br>\|<br>β-Glu (3 -> 1) |
| Rebaudioside B | H | β-Glu-β-Glu (2 -> 1)<br>\|<br>β-Glu (3 -> 1) |
| Rebaudioside C | β-Glu | β-Glu-α-Rha (2 -> 1)<br>\|<br>β-Glu (3 -> 1) |
| Rebaudioside D | β-Glu-β-Glu (2 -> 1) | β-Glu-β-Glu (2 -> 1)<br>\|<br>β-Glu (3 -> 1) |
| Rebaudioside E | β-Glu-β-Glu (2 -> 1) | β-Glu-β-Glu (2 -> 1) |
| Rebaudioside G | β-Glu | β-Glu-β-Glu (3 -> 1) |
| Rebaudioside M | β-Glu-β-Glu (2 -> 1)<br>\|<br>β-Glu (3 -> 1) | β-Glu-β-Glu (2 -> 1)<br>\|<br>β-Glu (3 -> 1) |
| Rebaudioside N | β-Glu-α-Rha (2 -> 1)<br>\|<br>β-Glu (3 -> 1) | β-Glu-β-Glu (2 -> 1)<br>\|<br>β-Glu (3 -> 1) |
| Rebaudioside O | β-Glu-α-Rha (2 -> 1)-β-Glu (3 -> 1)<br>\|<br>β-Glu (3 -> 1) | β-Glu-β-Glu (2 -> 1)<br>\|<br>β-Glu (3 -> 1) |

Glu: glucose
Rha: rhamnose

According to the current disclosure, steviol glycosides are produced in a process having at least two phases: first and second phases where a glucose-containing feed composition is provided to the medium in different modes of feeding in each phase, such as variable feeding and then constant feeding. A two phase feeding process as described herein can result in a growth rate that is slower in the second phase than in the first phase, and consequently increased steviol glycoside production rates, reduced fermentation times, and reduced biomass concentrations. The engineered yeast can have a set of enzymes that provide a pathway for the synthesis of steviol glycosides. For example, the process can produce steviol glycosides such as RebM and RebD.

The method of the disclosure can use various yeast host cells engineered to provide a pathway to one or more steviol glycosides. Such cells can be transformed with one or more DNA construct(s) encoding enzymes for steviol glycoside synthesis. Exemplary yeast that can be used for hosts for exogenous DNA constructs encoding steviol glycoside pathway enzymes, include, but are not limited to species of *Candida, Kloeckera (Hanseniaspora), Kluyveromyces, Lipomyces, Pichia (Hansenula), Rhodotorula, Saccharomycete, Saccharomyces, Schizosaccharomyces, Torulopsis, Torulaspora, Yarrowia,* and *Zygosaccharomyces*. Exemplary species are *Candida albicans, Pichia pastoris, Saccharomyces cerevisiae,* and *Schizosaccharomyces pompe,* and *Yarrowia lipolytica*. Further, host cells can also include genetic modifications other than those of the steviol glycoside pathway that may provide improved performance during fermentation.

An "engineered yeast" refers to yeast cells having at least one exogenous DNA sequence that is introduced into the cell, either integrated into the cell's genome or present on an extrachromosomal construct, such as a plasmid or episome. The term "exogenous" refers to a molecule, such as a nucleic acid, or an activity, such as an enzyme activity, that is introduced into the host yeast. An exogenous nucleic acid can be introduced into the yeast host by well-known techniques and can be maintained external to the hosts chromosomal material (e.g., maintained on a non-integrating vector), or can be integrated into the yeast's chromosome, such as by a recombination event. Generally, the genome of an engineered yeast is augmented through the stable introduction of one or more recombinant genes. An exogenous nucleic acid can encode an enzyme, or portion thereof, that is either homologous or heterologous to the yeast. An exogenous nucleic acid can be in the form of a "recombinant gene or DNA construct" referring to a nucleic acid that is in one or more ways manipulated through molecular techniques to be in a form that does not naturally exist.

The term "heterologous" (e.g., "non-native") refers to a molecule or activity that is from a source that is different than the referenced molecule or organism. Accordingly, a gene or protein that is heterologous to a referenced organism is a gene or protein not found in that organism. In the context of the disclosure, a "heterologous glycosyltransferase" refers to a glycosyltransferase polypeptide that is different from any glycosyltransferase polypeptide that may be native to the host organism. For example, a specific glycosyltransferase gene found in a first species and exogenously introduced into a host yeast organism that is different than the first species is "heterologous" to the host yeast.

The engineered yeast can use an auxotrophic marker suitable for selecting for a transformant having a nucleic acid encoding a steviol glycoside pathway enzyme. The host yeast can include modifications (deletions, and the like) in one or more genes that control auxotrophies, such as LYS2, LEU2, HIS3, URA3, URA5, and TRP1. Using a host cell having a desired genetic background for introduction of one or more exogenous genes, one or more gene construct(s) is introduced into a cell to integrate into the genome, or to be stably maintained and allow for expression. Methods for introducing a gene construct into a host cell include transformation, transduction, transfection, co-transfection, and electroporation. In particular, yeast transformation can be carried out using the lithium acetate method, the protoplast method, and the like. The gene construct to be introduced may be incorporated into a chromosome in the form of a plasmid, or by insertion into the gene of a host, or through homologous recombination with the gene of a host. The transformed yeast into which the gene construct has been introduced can be selected with a selectable marker (for example, an auxotrophic marker as mentioned above). Further confirmation can be made by measuring the activity of the expressed protein, or the production of a bioproduct such as a steviol glycoside.

The transformation of exogenous nucleic acid sequences including the steviol pathway genes can be confirmed using methods well known in the art. Such methods include, for example, nucleic acid analysis such as Northern blots or polymerase chain reaction (PCR) amplification of mRNA, or immunoblotting for expression of gene products, or other suitable analytical methods to test the expression of the introduced nucleic acid sequences or their corresponding gene product. It is understood by those skilled in the art that the exogenous nucleic acid is expressed in a sufficient amount to produce the desired product, and it is further understood that expression levels can be optimized to obtain sufficient expression using methods well known in the art and as disclosed herein.

The terpenoid compounds isopentenyl diphosphate (IPP) and dimethylallyl diphosphate (DMAPP) can serve as chemical precursors to steviol glycosides in an engineered yeast. Some organisms, including plants, insect, and some microbial species, have a mevalonate (MVA) pathway that converts acetyl-CoA through a series of chemical intermediates to IPP and DMAPP. Some organisms produce IPP and DMAPP through the non-mevalonate pathway (also known as the methyl D-erythritol 4-phosphate or MEP pathway) starting with glyceraldehyde-3-phosphate (G3P) and pyruvate (PYR).

The yeast *Saccharomyces cerevisiae* naturally expresses genes of the mevalonate pathway. Mevalonate pathway genes include: (a1) acetoacetyl CoA thiolase (EC 2.3.1.9), (b1) 3-hydroxy-3-methylglutaryl-coenzyme A (HMG-CoA) synthase (EC 4.1.3.5); (c1) HMG-CoA reductase (EC 1.1.1.34); (d1) mevalonate kinase (EC 2.7.1.36); (e1) phosphomevalonate kinase (EC 2.7.4.2); and (f1) mevalonate diphosphate decarboxylase (EC 4.1.1.33). Enzymes of the mevalonate pathway converts acetyl-CoA to IPP as follows: acetyl-CoA→acetoacetyl-CoA→3-hydroxy-3-methylglutaryl-CoA→mevalonate→mevalonate-5-phosphate→mevalonate-5-pyrophosphate→IPP. See also FIG. 1.

In some embodiments, the engineered yeast can include one or more modifications to increase the flux from acetyl-CoA to IPP and/or DMAPP, thereby providing an increased pool of IPP and/or DMAPP for use in a pathway to steviol. The modifications can include, for example, increasing expression or activity of one or more mevalonate pathway enzymes (a1)-(f1), such as by placing a nucleic acid encoding an enzyme that is homologous or heterologous to the yeast cell under the control of a promoter that provides increased expression, using multiple copies of the nucleic acid, and/or using a heterologous enzyme, a variant enzyme (e.g., one including one or more amino acid substitutions), or a variant heterologous enzyme that provides a higher level of enzymatic activity as compared to the native enzyme.

Alternatively, the non-mevalonate (MEP) pathway can be used to provide IPP and DMAPP as precursors to steviol glycoside production. The yeast *Saccharomyces cerevisiae* do not naturally express genes of the MEP pathway, but can optionally be engineered to provide MEP pathway genes. Theoretically, the MEP pathway is more energetically efficient generally because it loses less carbon as CO2 as compared to the MVA pathway (MEP pathway: 1 CO2/IPP; MVA pathway: 4 CO2/IPP; sugar as carbon source).

Figure 2:
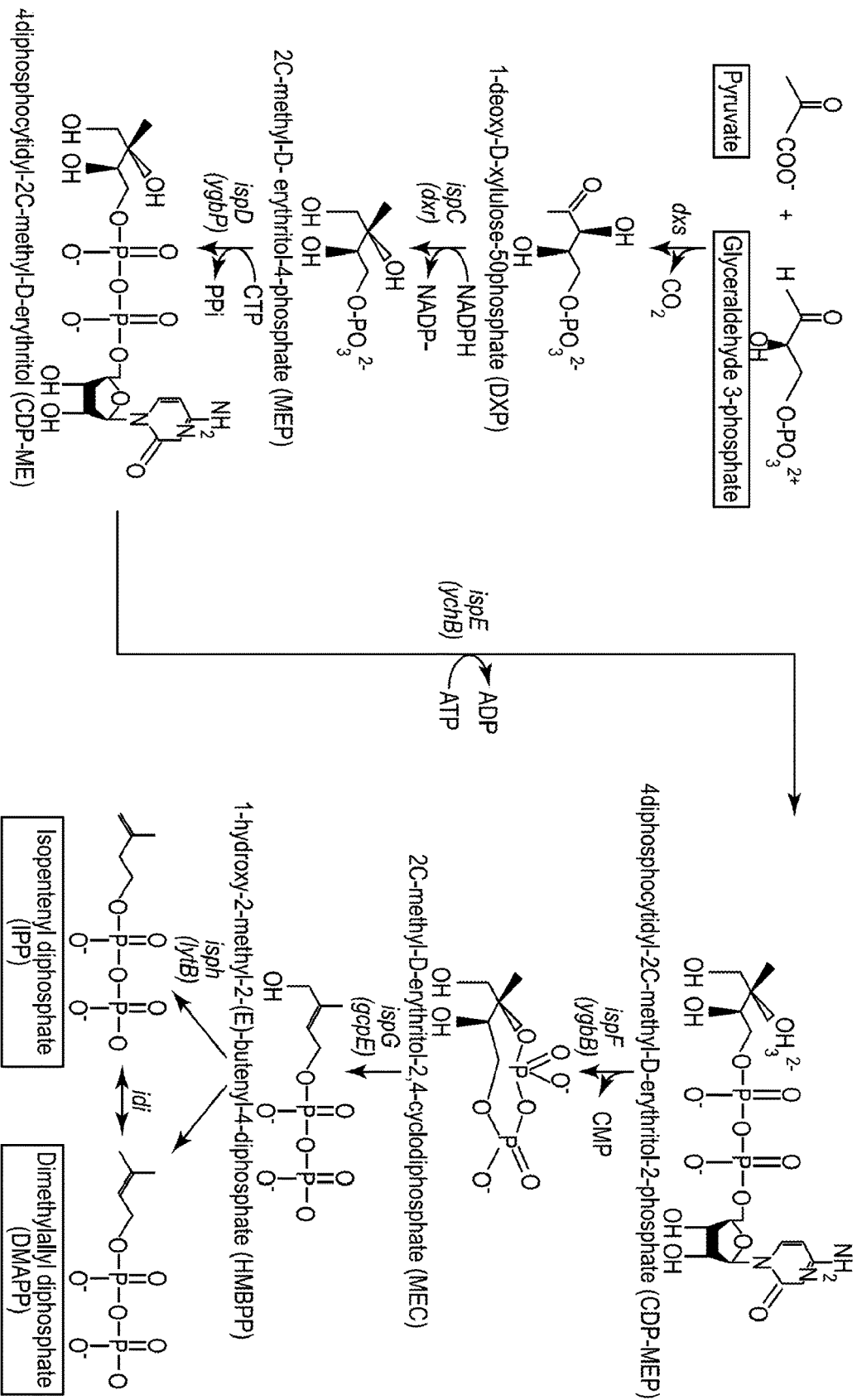
FIG. 2 shows a representative non-mevalonate pathway.

In particular, in the non-mevalonate (MEP) pathway compounds isopentenyl diphosphate (IPP), dimethylallyl diphosphate (DMAPP) are generated through a series of intermediates leading from glyceraldehydes-3-phosphate (G3P) and pyruvate (PYR), and a number of enzymes are responsible for this conversion. Enzymes involved in a biosynthetic pathway from G3P and PYR to IPP and DMAPP include (a2) 1-deoxy-D-xylulose-5-phosphate synthase (DXS), (b2) 1-Deoxy-D-xylulose-5-phosphate reductoisomerase (ispC)-, (c2) 4-diphosphocytidyl-2C-methyl-D-erythritol synthase (IspD), (d2) 4-diphosphocytidyl-2-C-methyl-D-erythritol kinase (IspE), (e2) 2C-Methyl-D-erythritol-2,4-cyclodiphosphate Synthase (IspF), (f2) 1-hydroxy-2-methyl-2-(E)-butenyl-4-diphosphate synthase (IspG), (g2) 4-hydroxy-3-methyl-2-(E)-butenyl-4-diphosphate reductase (IspH), and (h2) isopentenyl-diphosphate isomerase (IDI). See FIG. 2

The methods of the disclosure for producing steviol glycoside(s) by fermentation can use engineered yeast that have one or more genetic modifications to increase the flux from G3P and PYR to IPP and/or DMAPP, thereby providing an increased pool of IPP and/or DMAPP for use in a pathway to steviol. The modifications can include, for example, increasing expression or activity of one or more enzymes (a2)-(h2), such as by placing a nucleic acid encoding an enzyme that is heterologous to the yeast cell under the control of a promoter that provides increased expression, using multiple copies of the nucleic acid, and/or using a heterologous enzyme, a variant enzyme (e.g., one including one or more amino acid substitutions), or a variant heterologous enzyme that provides a high levels of enzymatic activity.

Figure 3:
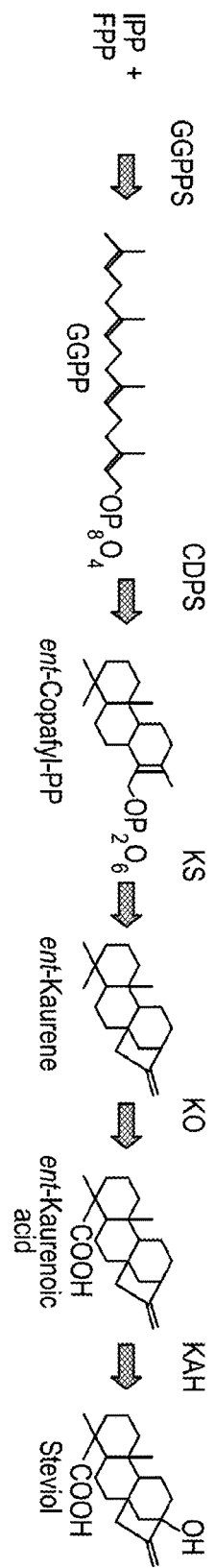
FIG. 3 shows a representative pathway for steviol production.

The methods of the disclosure for producing steviol glycoside(s) by fermentation can use engineered yeast can also include a pathway to convert IPP and/or DMAPP to steviol. For example, in some aspects the engineered yeast can include exogenous nucleic acids expressing the following enzymes: (a3) geranyl geranyldiphosphate synthase (GGPPS), (b3) copalyl diphosphate synthase (CPS), (c3) kaurene synthase (KS), (d3) kaurene oxidase (KO), and (e3) kaurenoic acid 13-hydroxylase (KAH). See FIG. 3 Enzymes of the mevalonate pathway converts IPP and/or DMAPP to steviol as follows: IPP/DMAPP→geranyl geranyldiphosphate→copalyl diphosphate→kaurene→kaurenoic acid→steviol. See FIG. 3 Exogenous nucleic acids encoding enzymes (a3)-(e3) that are heterologous to the yeast cell can be placed under the control of a promoter that provides increased expression, using multiple copies of the nucleic acid, and/or using a variant enzyme (e.g., one including one or more amino acid substitutions), or a variant heterologous enzyme that provides a high levels of enzymatic activity.

The methods of the disclosure for producing steviol glycoside(s) by fermentation can use engineered yeast having any pathway to convert steviol to a steviol glycoside. If more than one steviol glycoside pathway enzymes are present in the engineered yeast, the yeast may be able to produce different steviol glycosides. For example, the yeast may be able to produce two, three, four, five, six, seven, eight, nine, ten, or more than ten different steviol glycoside species.

Figure 4:
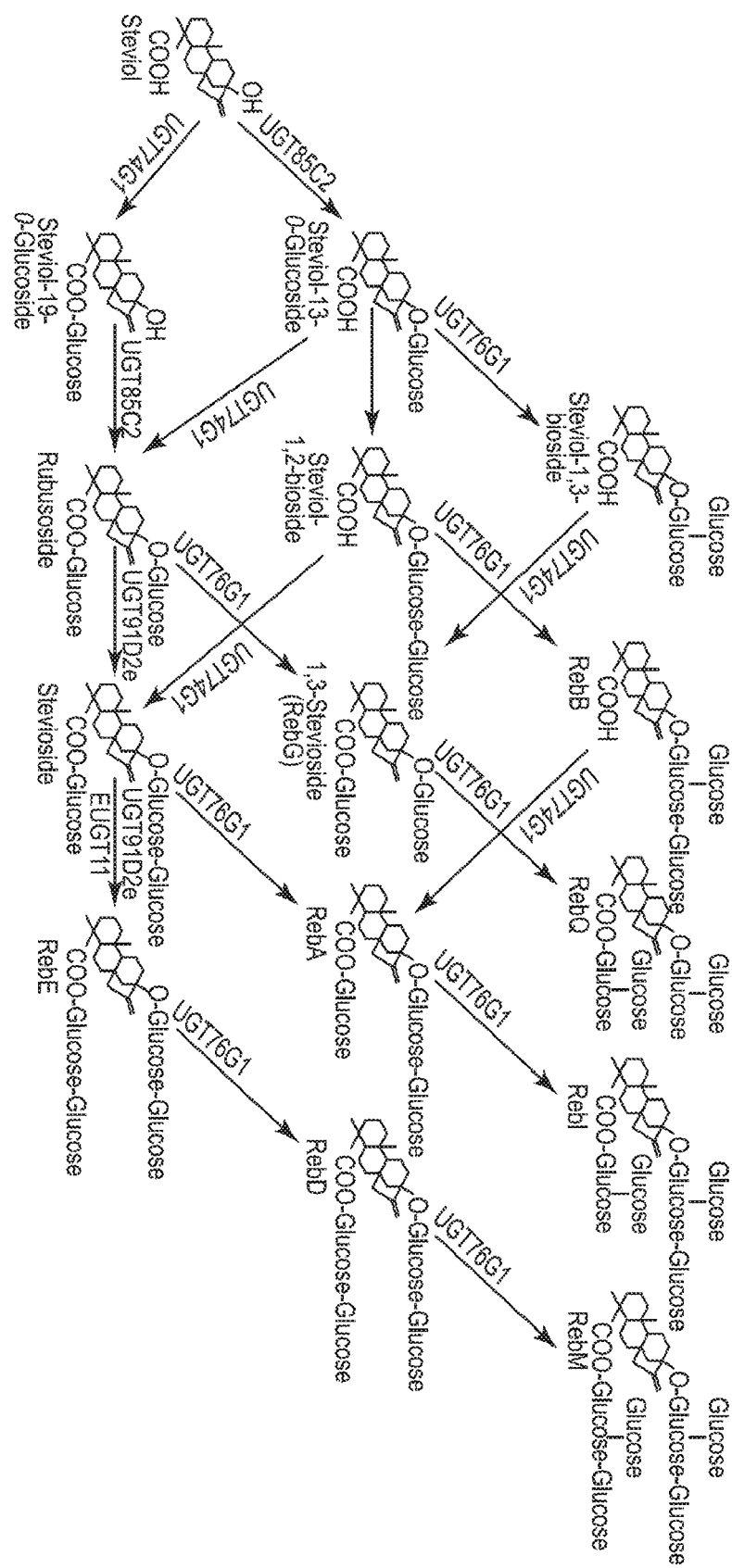
FIG. 4 shows representative pathways for the biosynthesis of steviol glycosides from steviol.

The steviol glycoside pathway can include one or more uridine diphosphate (UDP) glycosyltransferases (UGTs) that mediate the transfer of glycosyl residues from activated nucleotide sugars to acceptor molecules. In the case of a steviol glycoside pathway, a monosaccharide unit can be transferred to a hydroxyl or carboxyl moiety on a steviol or steviol glycoside molecule, or to a hydroxyl group on a glucose group that is attached to the steviol base. See FIG. 4. UGTs have been classified into families and subfamilies based on sequence homology. See Li, et al., 2001, J. Biol. Chem. 276:4338-4343. A superfamily of over 100 genes encoding UGTs, each containing a 42 amino acid consensus sequence, has been identified in the model plant *Arabidopsis thaliana*, and genes encoding UGTs have also been identified in several other higher plant species.

Exemplary UDP-glucosyltransferase can be any UDP-glucosyltransferase capable of adding at least one glucose unit to the steviol and or steviol glycoside substrate to provide the target steviol glycoside. In one embodiment, the engineered yeast can include one or more UDP-glucosyltransferase selected from group UGT74G1 (SEQ ID NO: 1), UGT85C2 (SEQ ID NO: 2), UGT76G1 (SEQ ID NO: 3), UGT91D2 (SEQ ID NO: 4), and also UGTs having substantial identity (e.g., >85%, >75%, >65%, >55%, >45% and >35%) to these polypeptides. An engineered yeast can include one or more exogenous nucleic acid molecule(s) that code for these UGTs.

The engineered yeast can also include one or more UGT and UDP-glucose recycling enzyme(s). An exemplary UDP-glucosyltransferase capable of adding at least one glucose unit to rubusoside to form stevioside is UGT91D2. An exemplary UDP-glucosyltransferase capable of adding at least one glucose unit to stevioside to form rebaudioside A is UGT76G1. An exemplary UDP-glucosyltransferase capable of adding at least one glucose unit to rebaudioside A to form rebaudioside D is UGT91D2. An exemplary UDP-glucosyltransferase capable of adding at least one glucose unit to rebaudioside D to form rebaudioside M is UGT76G1.

Exemplary publications that describe engineered microorganisms for steviol glycoside production and steviol glycoside pathway enzymes include, for example, US2014/0357588, WO2014/193934, WO2014/193888, and WO2014/122227, each of which are hereby incorporated by reference in their entirety.

In one embodiment, an engineered yeast useful for the production of steviol glycosides expresses the following enzymes: geranylgeranyl diphosphate synthase (GGPPS), ent-copalyl diphosphate synthase (CDPS), kaurene oxidase (KO), kaurene synthase (KS); steviol synthase (KAH), cytochrome P450 reductase (CPR), UGT74G1, UGT76G1, UGT91D2, UGT85C2 and a EUGT11. WO2014/122227 describes an engineered yeast strain that express these enzymes. The UDP-glucosyltransferases can be a gene encoding a polypeptide for example, UGT74G1 (SEQ ID NO: 1), UGT85C2 (SEQ ID NO: 2), UGT76G1 (SEQ ID NO: 3), UGT91D2 (SEQ ID NO: 4), and a EUGT11 (SEQ ID NO: 13); these genes encode polypeptides capable of carrying out a number of reactions such as a) a gene encoding a polypeptide capable of beta 1,2 glucosylation of the C2' of the 19-0 glucose of a steviol glycoside; (b) a gene encoding a polypeptide capable of beta 1,2 glucosylation of the CT of the 13-O-glucose of a steviol glycoside; (c) a gene encoding a polypeptide capable of beta 1,3 glucosylation of the C3' of the 19-O-glucose of a steviol glycoside; (d) a gene encoding a polypeptide capable of beta 1,3 glucosylation of the C3' of the 13-O-glucose of a steviol glycoside; (i) a gene encoding a polypeptide capable of glucosylation of the 13-OH of steviol or a steviol glycoside; (j) a gene encoding a polypeptide capable of glucosylation of the C-19 carboxyl of steviol or a steviol glycoside. For example, UGT85C2 carries out reaction (i); UGT74G1 carries out reaction (j); UGT91D2 carries out reactions (a; weakly), (b); UGT76G1 carries out reactions (c) and (d) EUGT11 carries out reactions (a), (b; less well).

The term "medium" refers to a liquid composition in which the engineered yeast or fungus can be maintained, can grow, can ferment, or combinations thereof. A "medium" may also be referred to as a "broth" or "cell culture," and terms such as "growth," "division," "respiration," and "fermentation" may be used to more specifically define the type of cellular activity that is occurring in the medium.

A medium can be defined with regards to the components present in the medium, and amounts thereof, such as (a) carbon sources, including carbohydrates such as glucose and starch products such as maltodextrin; (b) nitrogen sources, such as yeast nitrogen base, ammonium hydroxide, urea, ammonium sulfate, or any combination thereof; (c) salts, such as potassium phosphate (monobasic, dibasic), magnesium sulfate, sodium chloride, and calcium chloride; (d) vitamins, such as biotin, calcium pantothenate, folic acid, (myo)-inositol, nicotinic acid, p-aminobenzoic acid, pyridoxine HCl, riboflavin, thiamine HCL, and citric acid; and/or (e) trace metals such as boric acid, copper sulfate, cobalt chloride, calcium chloride, potassium iodide, ferric chloride, magnesium sulfate, manganese chloride, sodium molybdate, and zinc sulfate. Components in the medium can be defined on a dry weight basis. Further, the medium is water-based, or an "aqueous" composition. The medium can also be defined with regards to its pH, and biocompatible acids, bases, and buffers that are used to control the pH in the medium.

In exemplary embodiments, the concentration of glucose in the medium in steps (a) and (b) is kept in the range of about 0 g/L to about 5 g/L, or 0 g/L to about 2 g/L. In exemplary embodiments, the concentration of a nitrogen source (total amount) in the medium, such as yeast nitrogen base, ammonium hydroxide, urea, ammonium sulfate, yeast extract is in the range of about 5 g/L to about 40 g/L. In exemplary embodiments, the concentration of salts (total amount) in the medium, such as salts including magnesium sulfate in the range of about 0 g/L to about 12 g/L, and potassium phosphate in the range of about 0 g/L to about 22 g/L. In exemplary embodiments, the concentration of trace metals (total amount) in the medium is kept in the range of about 0 g/L to about 0.4 g/L, or 0 g/L to about 0.2 g/L.

A composition (a "feed composition") can be added to the medium that includes the engineered yeast to increase the volume of the medium, and as the engineered yeast grows in the medium, the amount of biomass. The feed composition can include components for yeast growth and fermentation to form a desired medium. The feed composition can include carbohydrate(s), a nitrogen source, such as ammonium hydroxide, urea, ammonium sulfate, yeast extract, or any combination thereof; salts, vitamins, and trace metals. The concentration of the components in the feed composition may be greater than the concentration of components in the medium so that when the feed composition is added it provides desired amounts of components in the medium suitable for fermentation of the engineered yeast.

Fermentation of the engineered yeast can be performed using starch and/or sugar containing plant material derivable from any plant and plant part, such as tubers, roots, stems, leaves and seeds. Starch and/or sugar-containing plant material can be obtained from cereal, such as barley, wheat, maize, rye, sorghum, millet, barley, potatoes, cassava, or rice, and any combination thereof. The starch- and/or sugar-containing plant material can be processed, such as by methods such as milling, malting, or partially malting. In some embodiments, the medium for steps (a) and (b) includes a treated starch. For example, the medium for growth and/or fermentation can include a partially hydrolyzed starch. The partially hydrolyzed starch can include high molecular weight dextrins and high molecular weight maltodextrins. A partially hydrolyzed starch product can be used that has amounts of starch and starch degradation products within desired ranges beneficial for steviol glycoside production.

Optionally, a starch degrading enzyme can be added to the medium that includes a starch material in order to increase the concentration of monomeric sugars such as glucose that can be utilized by the engineered yeast during the fermentation stage. Exemplary starch-degrading enzymes include amylolytic enzymes such as glycoamylase and amylase. In some embodiments, fermentable sugars such as fructose, sucrose, maltose, maltotriose, and the like can be included in the medium instead of or in addition to glucose.

In some optional modes of practice, fermentation can be carried out in medium that includes steviol-containing compounds. Such compounds can be directly used by the glucosyltransferases in the engineered yeast. For example, optionally, fermentation can be carried out in medium containing steviol-13-O-glucoside or steviol-19-O-glucoside. Using this medium, the microorganism may contain and express genes encoding a functional EUGT11, a functional UGT74G1, a functional UGT85C2, a functional UGT76G1, and a functional UGT91 D2.

Compounds such as rebaudioside A, rebaudioside D, and rebaudioside M may be obtained from the fermentation medium. As another option, fermentation can be carried out in medium containing rubusoside. Using this medium, the microorganism may contain and express genes encoding a functional EUGT11, a functional UGT76G1, and a functional UGT91D2. Compounds such as rebaudioside A, D, and M may be obtained from the medium following fermentation.

In some cases fermentation is carried out in industrial capacity fermenters in order to achieve commercial scale economic benefits and control. In an embodiment, the fermentation is carried out in a fermenter that has a capacity of about 10,000 liters or more.

The terms "first phase" and "second phase" (and optionally, "pre-phase," "third phase," "fourth phase," fifth phase," etc., if necessary) may be used to describe aspects of the method of producing steviol glycosides with regards to the medium. The term "stage" may also be used for "phase." The process includes two or more phases where the medium is treated differently in each phase, such as by adding a feed composition to the medium in a second, later, phase of the process in a mode that is different than a mode of adding the feed composition in the first, earlier, phase. The difference in mode of addition affects the growth of the engineered yeast, and production of the steviol glycosides during the process.

Prior to the first phase (in which cell growth is controlled by the first mode of adding), the cells can be cultured according a "pre-phase." The pre-phase can be a "seed/initial growth phase" in which cells are grown in a medium to become acclimated to the medium components (carbohydrates, nitrogen source, salts, vitamins, trace metals). In the pre-phase carbohydrate supply to the cells is not modulated as it is during the first and second phases, so the cells may grow at their maximum biological rate. For example, the cells in the pre-phase may be batch fed. As the cells become acclimated to the medium, the cells will enter a growth phase and increase in cell numbers. During the pre-phase, the engineered yeast can multiply by budding, referred to as yeast division.

For example, during the pre-phase a growth composition that includes carbohydrate(s), a nitrogen source, such as yeast nitrogen base, ammonium hydroxide, urea, ammonium sulfate, or any combination thereof, salts, vitamins, and trace metals can be added to medium that includes the engineered yeast in a batch process. In some modes of practice a composition is added to provide a medium that has ammonium hydroxide, urea, ammonium sulfate, or combinations thereof, as the sole nitrogen source. The same composition can be used as a feed composition in the subsequent first phase, where cell growth is controlled by the mode of addition of the feed composition to the medium.

Following the pre-phase, which is characterized by rapid cell growth and increase in biomass, the first phase (e.g., step a) can be commenced by regulating addition of the glucose containing composition according to the first mode of adding. The first phase can be described in various ways, such as by the how the feed solution is added to the medium and how the cells grow in response to that type of addition.

The mode of addition can affect the doubling times of the engineered yeast. The doubling times in the first phase can be greater (slower growth) than the doubling times in the pre-phase. During the first phase the biomass of the medium can increase, but it may increase at a rate that is lower than the increase seen in the pre-phase. The first phase can also be described in terms of how the cells grow as compared to the second phase, where feed solution is added to the medium in a second mode that is different than the first mode.

For example, in the first phase the yeast can be grown in a medium under conditions to achieve one or more growth rate(s). The growth rates may be controlled by controlling the feed rate of the feed medium to the fermenter to reach certain dilution rate(s)) that are within a first range that is greater than growth in the second phase. For example, in the seed/growth phase the growth rate ($\mu$) can be about 0.06 $h^{-1}$ or greater, such as a rate in the range of about 0.06 $h^{-1}$ to about 0.17 $h^{-1}$, or about 0.09 $h^{-1}$ to about 0.15 $h^{-1}$. Growth can be measured by optical density, for example at 600 nm. Growth rate can be controlled by adjusting the feed rate of the feed medium based on growth rate measurements, for example by increasing the feed rate to increase growth rate or by decreasing feed rate to decrease growth rate.

Optionally, the first phase can be described in terms of glucose concentration in the medium. For example, in some modes of practice, the first phase is started at a time when there is less than 3 g/L of glucose in the medium (glucose may be determined by using YS12700 Select Chemical Analyzer, Yellow Springs, Ohio). For example, the amount of glucose in the medium during the pre-phase can be monitored and when the concentration drops below 3 g/L, the first phase feeding can be started.

A desired growth rate in the first phase can be achieved by adding a composition comprising glucose to the medium according to a first mode. A "mode of feeding" refers to a way a feed composition that includes glucose is added to the medium having the engineered yeast. Modes of feeding include constant rates of feeding, non-constant rates of feeding, continuous addition of feed composition, bulk addition of feed composition, etc. In some modes of feeding, a feed composition is added to the medium at a non-constant rate of feeding during the first phase. For example, the non-constant rate of feeding can be a variable rate of feeding.

A variable rate of feeding refers to adding a feed solution to the medium at two or more different rates over a period of adding a feed solution to the medium. In some modes of practice, during a variable rate feeding, the rate decreases over a period of time. For example, in a growth phase of the process the feeding can change from a higher rate of feeding earlier in the growth phase to a lower rate of feeding later in the growth phase. This can be carried out by constantly decreasing rate of feeding, or can be carried out by a series of small decremental steps. In an optional mode of practice, a variable rate of feeding can include increasing the rate of feeding and then decreasing the rate of feeding.

A variable rate of feeding can be achieved using a variable rate addition system. Examples of such systems include a variable speed pump or a metering valve (such as a throttle valve) operably connected to a pump, which pump or valve can be utilized to vary the amount of feed composition introduced into the fermentation medium over time.

The first phase may also be explained with reference to one or more parameters associated with the medium, such as the period of time of the first phase, the temperature of the medium, the amount of biomass grown, and the pH of the medium. In some modes of practice, the first phase with a variable rate of feeding can be carried out for a period of time of about two hours or greater and up to about 40 hours. For example, the first phase can be about 10 hours or greater, such as a period of time in the range of about 10 hours to about 30 hours, or about 10 hours to about 24 hours. The first phase may encompass all or part of the lag phase of growth, and all or part of the log (exponential) phase of growth of the engineered yeast. After this period of time the mode of adding the feed composition including glucose to the medium can then be changed (e.g., to a constant rate of feeding in the second phase).

In exemplary modes of practice, in the first phase the medium is kept at a temperature in the range of about 25-35° C., or 28-32° C., and most preferably at about 30° C. Also, growth of the engineered yeast can be performed with aeration, and/or with agitation. Aeration conditions can have an effect on the amount of oxygen dissolved in the medium, and therefore the oxygen available to the engineered yeast. The amount of oxygen uptake by the engineered yeast can be controlled by the rate at which oxygen is supplied the formation of small oxygen bubbles in the medium, which can be achieved through agitation and/or sparging.

In the medium and during the first phase, the aeration can be performed. Aeration may be described in terms of dissolved oxygen transfer rate to the medium in units of mg $min^{-1}$ $liter^{-1}$. Aeration may also be described in terms of the dissolved oxygen (%). (For example, see Anderlei, T., and Büchs, J. (2000) Biochem. Engin. J. 3478:1-6). A sparging technique that promotes the formation of fine gas bubbles can be performed to provide desired aeration. In some modes of practice, during the first phase, agitation and aeration are increased, such as in a stepwise manner. Methods of the disclosure using a two phase feeding process can also reduce the aeration needs in the medium while still providing desired steviol glycoside production. In some modes of practice the dissolved oxygen is maintained at greater than 15%.

As used herein "biomass" refers to the weight of the engineered yeast, which can be measured in grams of dried cell weight per liter of medium (DCW/L). As another exemplary parameter, in some modes of practice, the first phase with a variable rate of feeding produces an amount of biomass of at least about 5 dcw/L. Preferably, the amount of biomass produced is in the in the range of about 5 g dcw/L to about 60 g dcw/L, about 20 g dcw/L to about 60 g dcw/L, or about 20 g dcw/L to about 40 g dcw/L.

As another example, in some modes of practice, the first phase with a variable rate of feeding is carried out at a pH of 6.0 or less, less than about 5.5, and preferably less than 5.2, such as in the range of about 4.0 to about 5.2. During the first phase the pH can be monitored to so that it stays within a desired, lower pH range, such as in the range of about 4.0 to 5.2. Acid or base can be added to the medium during the feeding to maintain the pH within a desired range.

After the first phase, the engineered yeast can enter the second phase, such as a "fermentation phase" where the mode of providing the feed composition is different than in the first phase. In the second phase the growth of the engineered yeast has at least slowed and are actively assimilating carbohydrate and producing steviol glycoside(s). As used herein "fermentation" is used to describe the phase of significant production of steviol glycoside(s), which can occur in fully aerobic, partially aerobic or anaerobic conditions. In partially aerobic conditions, both fermentative and respiratory pathways can be active, and some cell growth may occur. In partially aerobic conditions the amount of oxygen consumed can be less than during the seed/growth phase.

In the second phase, a feed composition with glucose can be added to the medium in a different mode than in the first phase. In some modes of practice, the first and second phases are carried out in the same vessel, wherein during the first phase a feed solution that includes glucose is added to the medium in the vessel at a variable rate, and then in the second phase the feed solution is added to the medium in the same vessel but at a constant rate.

In some modes of practice, in the second phase the feed composition is added to the medium at a constant feeding rate. For example, the constant rate of feeding is not greater than 10 g glucose/L media/h, and preferably at a constant rate of feeding in the range of 2 g glucose/L media/h to 10 g glucose/L media/h.

For example, in the second phase which includes fermentation and production of the steviol glycosides, the yeast can be grown in a medium under conditions to achieve one or more growth rate(s) that are within a range. For example, in the second phase the growth rate(s) can be about 0.09 $h^{-1}$ or less, such as a rate in the range of about 0.015 $h^{-1}$ to about 0.09 $h^{-1}$, or about 0.015 $h^{-1}$ to about 0.06 $h^{-1}$.

In some modes of practice, in the second phase with a constant rate can be carried out for a period of time to provide desired production of steviol glycosides. For example, the second phase can be started at a time of about 30 hours or later from the start of step (a), and then can be performed up to 130 hours from an from the start of step (a). The second phase may encompass all or part of the fermentation phase where the majority of steviol glycosides are produced. Preferably most of the steviol glycoside(s) (i.e., greater than 50%) are produced by the engineered yeast during the second phase. Methods of the disclosure including the two phase feeding provide a benefit with regards to fermentation, allowing up to about a 25% reduction, or even up to a 40% reduction in fermentation times as compared to a control process (e.g., a single phase fermentation).

Further, in some modes of practice, in the second phase with a constant rate of feeding can be controlled so the engineered yeast do not grow to a biomass amount of greater than 180 g dcw/L. Methods of the disclosure including the two phase feeding provide a benefit with regards to biomass production, allowing up to about a 25% reduction in the amount of biomass produced as compared to a control process with a single phase fermentation.

Further, in some modes of practice, during the second phase the medium can have a higher pH than the pH in the medium during the first phase. For example, at the start of, or during the second phase, a base can be added to the medium to increase the pH from a lower to a higher pH. The base can be present in the feed composition, or can be added separate from the feed composition for the second phase. For example, in the second phase the pH can be adjusted to about pH 5.8 or greater, or about pH 6.0 or greater, such as in the range of about pH 5.8 to about pH 7.5 or greater, or about pH 6.0 to about pH 7.0. During the second phase, the pH can be monitored (e.g., periodically or continuously) and adjustments to the medium can be made if the pH falls outside a desired range. For example, ammonium hydroxide can be added to the second medium if the pH drops below 6.0 or 5.8, so as to adjust the pH to about 6.0 or greater.

In exemplary modes of practice, fermentation and optionally growth in the second phase is performed at a temperature in the range of about 25-35° C., or 28-32° C., and most preferably at about 30° C. Also, fermentation and optionally growth of the engineered yeast in the second phase can be performed with aeration, and with agitation. Methods of the disclosure using a two phase feeding process can also reduce the aeration needs in the medium while still providing desired steviol glycoside production.

During fermentation, the medium can be monitored for the production of steviol glycosides. Fermentation can be stopped at a point where there is a desired steviol glycoside total amount and profile.

In some modes of practice, glucose feed rates of a fermentation producing steviol glycoside can be controlled based on variables such as Respiratory Quotient (RQ), oxygen uptake rate (OUR), carbon dioxide evolution rate (CER) or combinations thereof. These variables can be measured in the broth or off gas. Controlling the glucose feed rate by these variables (e.g., Respiratory Quotient (RQ)) can increase the production, can increase the yield, decrease biomass production and decrease ethanol production of the desired steviol glycosides such as rebaudiosides D and rebaudioside M. Controlling the glucose feed rates can also increase the consistency of the fermentation operation, namely reducing failure rates of batches and reducing overall system variability due to glucose feed rate or culture physiology.

RQ can be used to control glucose feed rate to prevent the toxic ethanol accumulation, a by-product of fermentative metabolism.

RQ is defined as the molar rate of carbon dioxide produced divided by the molar rate of oxygen consumed in the culture. RQ can be measured by analyzing the exhaust gas coming from the fermentor for content of carbon dioxide and oxygen. This metabolic parameter can be measured continuously or intermittently throughout the desired production phase. In some modes of practice, appropriate intervals for measurements are every four hours, two hours, hourly, half-hour, quarter-hour, ten minutes, five minutes, four minutes, three minutes, two minutes, or one minute. Time periods during measurements may vary with growth conditions, from initiating the culture through production of steviol glycosides. Exemplary periods for measurement and control are between 20 and 40 hours, between 10 and 60 hours, between 5 and 70 hours, and between 20 and 110 hours after initiating of the culturing in the fermentor.

In the presence of oxygen, yeast cells use aerobic metabolism, which is more efficient, e.g., more energy is obtained from a mole of glucose under aerobic metabolism than under fermentative metabolism.

The RQ of a medium producing only ethanol from glucose approaches infinity (since little or no oxygen is consumed, the denominator of RQ approaches zero), whereas for purely aerobic metabolism of glucose the RQ approaches the value of 1.0 (three moles of oxygen are consumed to produce 3 moles of carbon dioxide). Thus, values higher than 1 indicate a mixed metabolic condition where both aerobic and fermentative metabolism are taking place simultaneously. Typically, oxygen transfer rate and/or glucose feed rate (or the rate of feeding other carbohydrate(s)) can be adjusted using RQ as a feedback control variable to accomplish this mixed metabolism.

RQ can be measured in the exhaust gas stream from a fermentor. Any known and suitable method for ascertaining the molar concentration of oxygen consumed and carbon dioxide generated can be used. Exemplary techniques which may be used are mass spectrometry, infrared spectroscopy, and paramagnetic analysis. Exemplary software that may be used, for example with a mass spectrophotometer, include GasWorks from Thermo Scientific™.

In some embodiments, the RQ is maintained at about 0.5 to about 2.0. In some modes of practice, the RQ is maintained from about 0.9 to about 1.5, or about 1.0 to about 1.3. Maintaining the RQ in the disclosed ranges can result in improved steviol glycoside production. For example, some modes of practice result in improved Reb D and Reb M production.

When RQ is maintained in a narrow range from approximately 1.1 to approximately 2, ethanol accumulation stabilizes at levels that are not toxic. In some embodiments, the concentration of ethanol is maintained between about 5 g/L and 17 g/L. RQ ranges that may be desirable include about 1.08-2.0; about 1.08-1.85; about 1.08-1.65; about 1.08-1.45; about 1.08-1.35; about 1.08-1.25; about 1.08-1.2; and about 1.08-1.15. Other suitable RQ ranges include 1.08 to 1.35, and 1.15 to 1.25. In some embodiments, the glucose addition rate is adjusted to maintain the RQ in the about from 0.5 to about 2.0, from 0.9 to about 1.5, or from 1.0 to about 1.3.

RQ can be monitored and controlled during any desired portion of the fermentation, for example from 0 to 110 hours, from 20-40 hours, from 20-70 hours, from 20-90 hours, from 20-110 hours, or any other desired time period. In some embodiments, the RQ is monitored during phase II feeding or fermentation phase.

Thus, RQ can be manipulated and changed over time by addition of various carbon sources, by addition of various amounts of a carbon source, and by manipulation of the oxygen levels. In one embodiment, oxygen levels are manipulated by increasing or decreasing agitation. In another embodiment, the ratio of oxygen to nitrogen gas in a gas feed is controlled. Ways that the oxygen transfer rate can be adjusted include changing the air flow rate, the oxygen concentration, the cell density, the temperature, and/or agitation. In some embodiments, glucose or other fermentable sugar feed is modulated to affect the RQ. Other fermentable sugars which can be used in the feed include without limitation fructose, sucrose, maltose, and maltotriose. Feed rate or composition can be modulated to affect the RQ. The control of RQ may be manual or automatic.

The "total steviol glycosides" refers all the steviol glycosides present in the medium after a period of fermentation, which includes the amount of steviol glycosides in the liquid medium and obtainable from the engineered yeast. The steviol glycoside content can be expressed with regards to a total steviol glycosides amount in the medium, or the amount of one or more, but not all, steviol glycosides, in the medium. The amount of steviol glycosides in the composition can be expressed in relation to one another, or to the total amount of steviol glycosides, such as by a weight percentage of the total amount of steviol glycosides, or a ratio, or range of ratios, expressed as weight percent, or molar percent. The amount of steviol glycosides can also be expressed relative to a control sample, such as a control sample prepared by a process that does not include the first and second stages of feeding.

In some modes of practice, method of the disclosure provides improvement in the production of certain steviol glycosides, such as rebaudioside D and rebaudioside M. In some embodiments, a combined production rate of rebaudioside D and rebaudioside M is at least 0.02 g/L/h, 0.03 g/L/h, 0.04 g/L/h, 0.05, 0.06, 0.07, or 0.075 $g^{-1}L^{-1}$.

Methods of the disclosure can provide an improvement in the rate of steviol glycoside production during fermentation. For example, engineered yeast that are grown and fermented using the first and second phase method as described herein can exhibit an increase in the rate of steviol glycoside production that is about 1% or greater, about 2% or greater, about 3% or greater, about 5% or greater, about 7% or greater, about 10% or greater, about 12% or greater, or about 15% or greater, relative to the rate of steviol glycoside produced via an engineered yeast strain that is grown and fermented in a control process ($1^{st}$ phase $\mu=0.12$ $h^{-1}$; $2^{nd}$ phase 7.71 g glucose $L^{-1}h^{-1}$).

The phased feeding according to the disclosure can result in Reb D and Reb M production and increased production rates, increased yields, reduced fermentation times and reduced biomass concentrations.

Following the second phase wherein fermentation produces steviol glycoside(s), a composition containing one or more steviol glycoside(s) can be obtained from the medium using various techniques. In some embodiments, a compound such as permeabilizing agent can be added to the medium to enhance removal of the steviol glycosides from the cell and into the medium.

The medium can then be centrifuged or filtered to remove the engineered cells. The medium can optionally be treated to remove low molecular weight components (glucose, basic nutrients, and salts), such as by membrane dialysis. Depending on a desired use, a composition comprising one or more steviol glycoside compound(s) can be used.

After fermentation the engineered yeast can optionally be treated using a heat treatment method to enhance the recovery of steviol glycosides. After fermentation, but before any heat, treatment the medium may contain a suboptimal amount of the steviol glycosides, with the most of the desired steviol glycosides within the engineered yeast. To increase the recovery of steviol glycosides, in some modes of practice a composition, such as the medium at the higher pH in which the engineered yeast have been fermented, is heated to a temperature in the range from 50° C. to 95° C., or 70° C. to 95° C., for a period of time in the range of 5 minutes to 48 hours.

If it is desired to provide a composition with steviol glycosides in enriched or purified form, or where certain steviol glycosides are separated from one another, further purification can be carried out. Such enrichment or purification of steviol glycoside components can be carried out on the medium in which fermentation took place, or the medium can then be dried down prior to purification. For example, medium can be dried down using lyophilization to form a dry composition (e.g., powder or flakes) including steviol glycosides that can be subsequently processed.

As used herein, the term "total steviol glycosides" (TSG) is calculated as the sum of the content of all steviol glycosides in a composition on a dry (anydrous) basis.

In some modes of practice, dried fermentation broth enriched for steviol glyosides is used as the starting material for purification. For example, a solvent or solvent combination can be added to the dried fermentation broth to dissolve or suspend material that includes the steviol glycosides. An exemplary combination for dissolving the steviol glycosides is a mixture of water and an alcohol (e.g., 50:50 ethanol:water). To facilitate dissolving or suspending, the dried broth materials can be heated at a temperature above room temperature, such as in the range of 40° C.-60° C. Mechanical disruption of the dried broth materials can also be performed, such as by sonication. The dissolved or suspended broth materials can be filtered using a micron or sub-micron prior to further purification, such as by preparative chromatography.

Dried fermentation broth enriched for steviol glycoside compounds can be subjected to purification, such as by reverse phase liquid chromatography. A suitable resin can be used to retain steviol glycoside compounds in the column, with removal of hydrophilic compounds which get washed through the column with a liquid such as water. Elution of steviol glycosides from the column can be accomplished a suitable solvent or solvent combination such as acetonitrile or methanol.

Elution of steviol glycosides from a reverse phase column can yield a composition which can be useful for any one of a variety of purposes. For example, a purified steviol glycoside composition can be used as a sweetener composition for oral ingestion or oral use. The composition can be defined with regards to the steviol glycosides in the composition.

Steviol glycoside-producing *S. cerevisiae* strains were constructed using methods as described in WO 2011/153378, WO 2013/022989, WO 2014/122227, and WO 2014/122328, each of which is incorporated by reference in their entirety. The following sequences were used for construction of a parent strain (Strain A): a recombinant gene encoding a *Synechococcus* sp GGPPS polypeptide (SEQ ID NO:6), a recombinant gene encoding a truncated *Zea mays* CDPS polypeptide (SEQ ID NO:7), a recombinant gene encoding an *Arabidopsis thaliana* KS polypeptide (SEQ ID NO:8), a recombinant gene encoding a recombinant *Stevia rebaudiana* KO polypeptide (SEQ ID NO:9, SEQ ID NO:10), a recombinant gene encoding an *Arabidopsis thaliana* ATR2 polypeptide (SEQ ID NO:11, SEQ ID NO:12), a recombinant gene encoding an *Oryza sativa* EUGT 11 polypeptide (SEQ ID NO:13), a recombinant gene encoding an SrKAHe1 polypeptide (SEQ ID NO:14, SEQ ID NO:15), a recombinant gene encoding an *Stevia rebaudiana* CPR8 polypeptide (SEQ ID NO:16, SEQ ID NO:17), a recombinant gene encoding an *Stevia rebaudiana* UGT85C2 polypeptide (SEQ ID NO:2), a recombinant gene encoding an *Stevia rebaudiana* UGT74G1 polypeptide (SEQ ID NO:1), a recombinant gene encoding an *Stevia rebaudiana* UGT76G1 polypeptide (SEQ ID NO:3), and a recombinant gene encoding an *Stevia rebaudiana* UGT91D2 variant (or functional homolog), UGT91D2e-b, (SEQ ID NO:4) polypeptide produced steviol glycosides.

The UGT91D2e-b variant of UGT91D2 (SEQ ID NO:5 from PCT/US2012/050021) includes a substitution of a methionine for leucine at position 211 and a substitution of an alanine for valine at position 286. (Additional variants, except T144S, M152L, L213F, S364P, and G384C variants, described in Table 12 and Example 11 of PCT/US2012/050021, which is hereby incorporated by reference in its entirety, could be used.) GeneArt codon-optimized sequence encoding a *Stevia rebaudiana* UGT91D2e-b with the amino acid modifications 1,211M and V286A (SEQ ID NO:4 for amino acid sequence; codon optimized nucleotide sequence is set forth in SEQ ID NO:5).

Strain B is derived from the parent strain described above and additionally includes a codon-optimized CPR1 from *Stevia rebaudiana* (SEQ ID NO:18 corresponding to amino acid SEQ ID NO:19).

Example 1

Production of Reb D and Reb M in a Two-Phase Feeding Process

For inoculum preparation, the yeast strain B was cultured in 150 mL of seed flask medium in 1 liter shake flasks at 250 rpm and 30° C. for 20-24 hours.

TABLE 1

Seed Flask Medium

| Component | Formula | Concentration | Units |
|---|---|---|---|
| Biospringer D251 yeast extract | | 7.5 | g/L |
| Glucose monohydrate | $C_6H_{12}O_6$* $H_2O$ | 22.0 | g/L |

For the fermentation, 75 mL of seed culture was transferred into initial fermentation medium, as in Table 2, with an initial volume of 0.75 liters (38.5% of tank level). Fed batch fermentations were carried out in 2L New Brunswick BioFlo310 fermenters. Fermentation was controlled at pH 5.0 with 12% $NH_4OH$ and temperature was maintained at 30° C. throughout. The air flow rate was 1.75 SLPM and agitation rate was 1200 rpm throughout the fermentation.

Glucose concentration was kept limited by controlling flow rates of fermentation feed medium. A 2-phase feeding strategy involved an initial exponential phase (feed phase I) beginning at 12 hours (after inoculating the fermenter) with a growth rate of u=0.12 $h^{-1}$ or higher while the feed phase II started in the range of 35-39 hours with constant flow rates. The phase II feeding involved constant feeding in the range of 14.4 to 22.96 g glucose/L broth/h. Feeding was continued until 1.0 liter of fermentation feed medium was delivered. Antifoam, Ivanhoe 1163B, was added to the feed medium at 1.3 g/L and additional bolus additions of 5 wt % antifoam solution were added as needed.

The medium was based on Verduyn et al (Verduyn C, Postma E, Scheffers W A, and Van Dijken J P. Yeast. 1992 Jul.; 8(7):501-17) with modifications as described in tables 2 and 3.

TABLE 2

| Component | Formula | Concentration | Units |
|---|---|---|---|
| Initial Fermentation Medium | | | |
| Glucose monohydrate | $C_6H_{12}O_6 * H_2O$ | 22.0 | g/L |
| Ammonium sulfate | $(NH_4)_2SO_4$ | 5.0 | g/L |
| Monobasic potassium phosphate | $KH_2PO_4$ | 3.0 | g/L |
| Magnesium sulfate heptahydrate | $MgSO_4 * 7 H_2O$ | 0.5 | g/L |
| Trace metals stock | | 10.0 | ml/L |
| Vitamin stock | | 12.0 | ml/L |
| Trace Metals Stock Solution | | | |
| Disodium edetate | $C_{10}H_{14}N_2Na_2O_8 * 2H_2O$ | 15 | g/L |
| Zinc sulfate heptahydrate | $ZnSO_4 * 7H_2O$ | 4.5 | g/L |
| Manganese (II) chloride tetrahydrate | $MnCl_2 * 4H_2O$ | 1.026 | g/L |
| Cobalt (II) chloride hexahydrate | $CoCl_2 * 6H_2O$ | 0.32 | g/L |
| Copper (II) sulfate heptahydrate | $CuSO_4 * 5H_2O$ | 0.3 | g/L |
| Sodium molybdate dihydrate | $Na_2MoO_4 * 2H_2O$ | 0.4 | g/L |
| Calcium chloride dihydrate | $CaCl_2 * 2H_2O$ | 3 | g/L |
| Iron (II) sulfate heptahydrate | $FeSO_4 * 7H_2O$ | 3 | g/L |
| Boric acid | $H_3BO_3$ | 1 | g/L |
| Potassium iodide | KI | 0.1 | g/L |
| Vitamin Stock Solution | | | |
| d-Biotin | $C_{10}H_{16}N_2O_3S$ | 50 | mg/L |
| Calcium pantothenate | $C_{18}H_{32}CaN_2O_{10}$ | 1000 | mg/L |
| Nicotinic acid | $C_6H_5NO_2$ | 1000 | mg/L |
| Thiamine hydrochloride | $C_{12}H_{17}ClN_4OS \cdot HCl$ | 1000 | mg/L |
| Pyridoxine hydrochloride | $C_8H_{11}NO_3 \cdot HCl$ | 1000 | mg/L |
| p-aminobenzoic acid | $C_7H_7NO_2$ | 200 | mg/L |
| myo-inositol | $C_6H_{12}O_6$ | 25000 | mg/L |

TABLE 3

| Component | Formula | Concentration | Units |
|---|---|---|---|
| Fermentation Feed Medium | | | |
| Glucose monohydrate | $C_6H_{12}O_6 * H_2O$ | 660 | g/L |
| Antifoam | | 1.3 | g/L |
| Potassium sulfate | $K_2SO_4$ | 4.2 | g/L |
| Sodium sulfate | $Na_2SO_4$ | 0.336 | g/L |
| Magnesium sulfate heptahydrate | $MgSO_4 * 7H_2O$ | 6.12 | g/L |
| Monobasic potassium phosphate | $KH_2PO_4$ | 10.8 | g/L |
| Trace metal stock | | 14.4 | mL/L |
| Vitamin stock | | 14.4 | mL/L |

Quantification of steviol glycoside can be carried out by high performance liquid chromatography (HPLC) analysis as described below, and compared against calibration curves obtained using authentic standards purchased from Chromadex.

100 µL of the fermentation media were pipetted into a 2 mL microcentrifuge tube. 900 µL of 61% methanol (extraction solvent) was added into the 2 ml microcentrifuge tube and agitated by placing on a sample rotator for 10 min to extract the steviol glycosides. The samples were then centrifuged at 10K rpm in a microcentrifuge for 3 min and the clarified supernatant was pipetted into an autosampler vial for analysis.

UHPLC Method for Glycoside Separation

The steviol glycosides were separated using two Agilent SB-C18 RRHD columns in series (2.1 mm×150 mm, 1.8 um) with a stem filter assembly from Optimize Technologies installed as a pre-column filter. The mobile phase used was channel A: 0.01% trifluroacetie acid (TFA) in water and channel B acetonitrile. The flow rate was 0.38 mL/min, the column temperature was 65° C. and the detection was performed at ultraviolet absorption of 210 nm. The gradient elution profile is shown below:

| Time | % Channel A | % Channel B |
|---|---|---|
| 0 | 85 | 15 |
| 0.5 | 85 | 15 |
| 30 | 75 | 25 |
| 40 | 65 | 35 |
| 49 | 47 | 53 |
| 49.1 | 0 | 100 |
| 58 | 0 | 100 |
| 58.1 | 85 | 15 |
| 62 | 85 | 15 |

Calibration was performed using Reb A (98.85% purity) from Cargill, Inc lot 1008-005 in 55% MeOH at the following concentrations: 0.35, 0.175, 0.07, 0.035, 0.014, 0.007 mg/mL. All glycosides are quantitated off of the Reb A curve. Experimental correction factors for Reb D, Reb M, and Reb B were determined against Reb A while all other analytes are corrected by molecular weight.

Cell dry weight (biomass) is measured by filtering broth through a 0.45 micron filter and washing with 3 volumes of water and dried in a 105 oven for 18 hours.

TABLE 4

Increased glucose medium feed rates in both phase I and phase II feedings of the 2 phase feeding regime

| Phase I feed rate (mu in h$^{-1}$) | Phase II feed rate g dx/L/h | Reb D conc g/L | Reb M conc g/L | Reb DM conc g/L | RebDM Rate mg/L/h | RebD/rebM ratio | Fermentation Time hours | Biomass conc g/L | Reb DM Yield g/g Dx*100 |
|---|---|---|---|---|---|---|---|---|---|
| 0.12 | 7.71 | 1.08 | 1.89 | 2.97 | 25.2 | 0.57 | 117.9 | 114.4 | 0.96 |
| 0.15 | 10.5 | 0.85 | 1.67 | 2.52 | 27.8 | 0.5 | 90.75 | 111.4 | 0.82 |
| 0.18 | 12.3 | 0.49 | 0.99 | 1.48 | 19.5 | 0.49 | 75.8 | 90.3 | 0.48 |

Example 2

For inoculum preparation, the yeast strain B was cultured as described in Example 1 using the seed flask medium of Table 1, Example 1. The fermentation, the initial fermentation medium and the fermentation feed medium were as described in Example 1.

TABLE 5

| n = | Treatment | Phase I rate ($\mu$ in h$^{-1}$) | Length of phase I (hrs) | Phase II rate (g Dx/L/hr) | Reb D g/L | Reb M g/L | Reb DM g/L | Reb DM Yield g/g Dx*100 | Reb DM Rate g/L/h | D/M Ratio | Biomass g DCW/L |
|---|---|---|---|---|---|---|---|---|---|---|---|
| 1 | Control (phase II feed rate A) | 0.12 | 23 | 7.71 | 1.38 | 2.41 | 3.79 | 1.23 | 0.031 | 0.57 | 101.8 |
| 2 | Phase II feed rate B | 0.12 | 12 | 2.83 | 1.26 | 1.79 | 3.05 | 1.69 | 0.025 | 0.71 | 97.8 |
| 2 | Phase II feed rate C | 0.12 | 16 | 4.51 | 1.45 | 1.97 | 3.42 | 1.76 | 0.028 | 0.74 | 101.6 |
| 1 | Batch (all glucose included at start) | n/a | n/a | n/a | 0.07 | 0.06 | 0.13 | 0.04 | 0.001 | 1.13 | 9.8 |

The phase I feed rate is kept constant and the feed phase II rate are variable but lower than used in Example 1. The data above shows improved yields with lower phase II feeding rates.

Example 3

For inoculum preparation, the yeast strain C was cultured as described in Example 1 using the seed flask medium of Table 1, Example 1. The initial fermentation medium unlike Example 1 did not include cobalt, molybdate and borate, only vitamin and trace minerals were added in the initial fermentation medium and not in the fermentation feed medium.

Improved yield with lower feeding rates, were observed as were higher rate with faster feeding (control).

Example 4

Production of Reb D and Reb M in Fed Batch Fermentation with Feedback Control of Glucose Feeding Based on Real Time Respiratory Quotient For inoculum preparation, the yeast strain B was cultured as described in Example 1 using the seed flask medium of Table 1, Example 1.

For the fermentation, 75 mL of seed culture was transferred into initial fermentation medium as described in Table

TABLE 6

| Treatment (phase I/phase II feeding) | Replicates | Phase I rate $\mu$ in h$^{-1}$ | Length of phase I hrs | Phase II feed rate g Dx L$^{-1}$ h$^{-1}$ | Reb D g/L | Reb M g/L | Reb D + Reb M g/L | Reb D + Reb M Yield g/g Dx*100 | Reb D + Reb M Rate g L$^{-1}$ h$^{-1}$ | Reb D/ Reb M ratio | Fermentation time hours | Biomass g DCW/L |
|---|---|---|---|---|---|---|---|---|---|---|---|---|
| u = 0.12/7.71 g Dx/L/h | n = 3 | 0.12 | 23 | 7.71 | 1.39 | 4.55 | 5.95 | 1.98 | 0.050 | 0.30 | 119.2 | 91.6 |
| u = 0.11/6.77 g Dx/L/h adjusted up to 7.52 g Dx/L/h stepwise | n = 3 | 0.11 | 25 | 6.77-7.52 | 1.43 | 4.67 | 6.10 | 2.02 | 0.049 | 0.31 | 124.0 | 93.5 |
| u = 0.11/6.77 g Dx/L/h to end of fermentation | n = 2 | 0.11 | 25 | 6.77 | 1.82 | 4.80 | 6.62 | 2.16 | 0.047 | 0.38 | 141.2 | 92.0 |

2 of Example 1 with a starting volume of 0.75 liters. Temperature was maintained at 30° C. throughout. The air flow rate was 1.75 SLPM and the agitation rate was automatically controlled to increase in a stepwise manner from 400 to 900 rpm during the fermentation. The pH was controlled at pH 5.0 with 12% NH4OH.

The medium was based on Verduyn et al (Verduyn C, Postma E, Scheffers W A, Van Dijken J P. Yeast. 1992 Jul.; 8(7):501-17) with modifications as described in Tables 2 and 3 of Example 1. For the urea treatments, ammonium sulfate was increased to 15 g/L in the initial fermentation medium and urea was added to 39 g/L in the fermentation feed medium.

Since *Saccharomyces cerevisiae* is a Crabtree positive organism, it makes ethanol in the presence of very low levels of glucose, thus the concentration of glucose was kept limiting by controlling flow rates of fermentation feed medium, (as described in Table 3 of Example 1) to allow growth while minimizing ethanol production.

For the two phase feeding regime, an initial exponential phase (feed phase I) began at 10 hours with a growth rate of $\mu$=0.12 l/h while the second phase of feeding (or feed phase II) started at 33 hours with a constant flow rate of 0.180 mls/minute. Feeding was continued until a final volume of 1.95 liters was obtained by 120 hours.

The treatment with respiratory quotient (RQ) based feedback control of feeding involved typical exponential feeding for the feed phase I. Then, at 39 hours, in the feed phase II of feeding, feedback control of glucose medium addition was measured on and feeding was then controlled by real time measurements of RQ by off-gas mass spectrometry analysis of oxygen and carbon dioxide concentrations in off-gas of fermentor vs. reference gas (air) with a Thermo Scientific Prima Pro Process MS instrument. The algorithm controlling feeding was designed to keep RQ between 1.05 and 1.25. RQ was calculated (by the mass spectrophotometer software by Thermo Scientific™ GasWorks) by dividing carbon dioxide evolution rate (CER) by oxygen uptake rate (OUR) using the calculation:

$$\text{OUR (mmol/L/h)} = (F(L/\text{min}) \times (\% O_{2in} - \% O_{2out}) \times 60 \text{ min/h} \times 1000 \text{ mmol/mol}) / (100 \times 24.45 \text{ L/mol} \times \text{fermentor volume (L)})$$

CER calculation:

$$\text{CER (mmol/L/h)} = (F(L/\text{min}) \times (\% CO_{2in} - \% CO_{2out}) \times 60 \text{ min/h} \times 1000 \text{ mmol/mol}) / (100 \times 24.45 \text{ L/mol} \times \text{fermentor volume (L)})$$

$$RQ = OUR/CER \text{ (a unitless ratio)}$$

Reb D and Reb M yields on glucose were calculated based on total glucose utilized. Yield of Reb D and Reb M on biomass was based on cell dry weight. Biomass determination of cell dry weights was based on the filtration/oven method, which is commonly known in the art.

TABLE 7

Results Summary for Respiratory Quotient Based Feed Back Control

| Treatment | Reb D (% of control) | Reb M (% of control) | Yield of product on glucose(% of control) | Yield of product on biomass(% of control) | Overall Specific Productivity (% of control) | Off-gas Ethanol (% of control during 60 h to 132 h) |
|---|---|---|---|---|---|---|
| Normal 2 phase feeding | 100.0 | 100.0 | 100.0 | 100.0 | 100.0 | 100.0 |
| RQ control of feeding | 80.1 | 123.7 | 107.0 | 130.7 | 113.5 | 34.0 |

"Normal 2-phase feeding" is 1st phase: $\mu = 0.12$ h$^{-1}$; 2nd phase = 7.71 g L$^{-1}$ h$^{-1}$.

Example 5

For inoculum preparation, the yeast strain C was cultured as described in Example 1 using the seed flask medium of Table 1, Example 1. The initial fermentation medium unlike Example 1 did not include cobalt, molybdate and borate, only vitamin and trace minerals were added in the initial fermentation medium and not in the fermentation feed medium.

TABLE 8

| Treatment | Phase I rate u in 1/h | Length of phase I hrs | Phase 2 rate g DX/L/h | Reb D g/L | Reb M g/L | Reb D + Reb M g/L | Reb D + Reb M Yield g/g Dx*100 | Reb D + Reb M Rate g L$^{-1}$ h$^{-1}$ | Reb D/ Reb M ratio | Fermentation time hours | Biomass g DCW/L |
|---|---|---|---|---|---|---|---|---|---|---|---|
| 2 phase scheduled feeding (control) | 0.12 | 23 | 7.71 | 1.36 | 4.48 | 5.84 | 1.95 | 0.046 | 0.30 | 127.3 | 98.2 |
| RQ target = 1.1 | 0.12 | 23 | RQ = 1.1 | 0.91 | 4.23 | 5.14 | 1.67 | 0.055 | 0.21 | 94.8 | 104.8 |
| RQ target = 1.3 | 0.12 | 23 | RQ = 1.3 | 0.89 | 3.95 | 4.84 | 1.58 | 0.071 | 0.22 | 67.8 | 123.4 |
| RQ target = 1.5 | 0.12 | 23 | RQ = 1.5 | 0.97 | 4.12 | 5.09 | 1.65 | 0.077 | 0.23 | 65.7 | 118.4 |

The respiratory quotient (RQ, a unitless ratio) equals carbon dioxide evolution rate (CER, mmol/L/h) divided by oxygen uptake rate (OUR, in mmol/L/h). Respiratory quotient (RQ) targets were achieved by an algorithm in BioCommand software that increased or decreased glucose feed rate based on the RQ value from real-time off gas monitoring of carbon dioxide and oxygen in the exit gas of fermentation. RQ feedback control was only used in phase II of the two phase feeding.

What is claimed is:

1. A method for producing one or more steviol glycoside(s), the method comprising steps of:

(a) growing engineered yeast capable of producing the one or more steviol glycoside(s) in a medium, wherein the engineered yeast is grown at one or more growth rate(s) within a first range; and wherein a composition comprising glucose is added to the medium according to a first mode; and (b) fermenting the medium with the engineered yeast to produce the one or more steviol glycoside(s), wherein during fermenting, a composition comprising glucose is added to the medium according to a second mode that is different than the first mode, and during fermenting the yeast grown at one or more growth rate(s) within a second range, wherein the second range is less than the first range;

wherein the growth rate in step (a) is 0.06 $h^{-1}$ or greater;

wherein the growth rate in step (b) is 0.09 $h^{-1}$ or less;

wherein step (a) is started at a time when there is less than 3 g/L of glucose in the medium; and wherein step (a) is performed up to a time of 40 hours from the start of step (a) time;

wherein the one or more steviol glycoside(s) comprise rebaudioside M, rebaudioside D, or both rebaudioside M and rebaudioside D; and wherein the engineered yeast is a species of *Saccharomyces*.

2. The method of claim 1, wherein in step (a) the first range is 0.06 $h^{-1}$ to 0.17 $h^{-1}$.

3. The method of claim 1, wherein in step (b) the second range is 0.015 $h^{-1}$ to 0.09 $h^{-1}$.

4. The method of claim 1, wherein the growth rate in step (b) is in the range of 50-90% of a maximum growth rate in step (a).

5. The method of claim 1, wherein in step (a) the composition comprising glucose is added to the medium according to the first mode which is a non-constant rate of feeding.

6. The method of claim 1, wherein in step (b) the composition comprising glucose is added to the medium according to the second mode which is a constant rate of feeding.

7. The method of claim 6, wherein the constant rate of feeding is in the range of 2 g glucose/L media/h to 10 g glucose/L media/h.

8. The method of claim 1, wherein in step (b) a base is added to provide the medium with a pH that is higher than the pH of the medium in step (a).

9. The method of claim 8, wherein in step (b) the pH of the medium is 6.0 or greater.

10. The method of claim 1, wherein step (b) is performed at a time of 30 hours or later from the start of step (a).

11. The method of claim 1, wherein in step (a) the engineered yeast are grown to a biomass amount of at least 5 g dcw/L.

12. The method of claim 11, wherein in step (a) the engineered yeast are grown to a biomass amount in the range of 20 g dcw/L to 60 g dcw/L.

13. The method of claim 1, wherein in step (b) the engineered yeast do not grow to a biomass amount of greater than 180 g dcw/L.

14. The method of claim 1, wherein the engineered yeast is *Saccharomyces cerevisiae*.

15. The method of claim 1, wherein during step (a) the concentration of glucose is not greater than 5 g/L in the medium.

16. The method of claim 1, wherein during step (b) the concentration of glucose is not greater than 5 g/L in the medium.

17. The method of claim 1, further comprising a step of:

(c) measuring respiratory quotient (RQ) of the engineered yeast at step (b) of claim 1 to determine if the RQ is within a range of from about 0.5 to about 2.0;

(d) adjusting the glucose addition rate of the second mode when the RQ is outside of the RQ range; and (e) repeating steps (c) and (d) throughout the step of fermenting the medium with the engineered yeast cells.

* * * * *